United States Patent
Gresch et al.

(10) Patent No.: US 10,779,462 B2
(45) Date of Patent: Sep. 22, 2020

(54) CALIBRATING AN ACTUATOR FOR SETTING A SEED DEPTH FOR A ROW UNIT ON A PLANTER

(71) Applicant: Deere & Company, Moline, IL (US)

(72) Inventors: Valentin Stefan Gresch, Ensheim (DE); Cary S. Hubner, Geneseo, IL (US); Christian Waibel, Mannheim (DE); Philipp Benz, Baden-Wuerttemberg (DE); Tobias Meilwes, Erlangen (DE); Robert Laga, Dresden (DE)

(73) Assignee: Deere & Company, Moline, IL (US)

( * ) Notice: Subject to any disclaimer, the term of this patent is extended or adjusted under 35 U.S.C. 154(b) by 61 days.

(21) Appl. No.: 15/783,258

(22) Filed: Oct. 13, 2017

(65) Prior Publication Data
US 2019/0110391 A1    Apr. 18, 2019

(51) Int. Cl.
| | | |
|---|---|---|
| *A01C 7/20* | (2006.01) | |
| *A01C 5/06* | (2006.01) | |
| *A01B 63/00* | (2006.01) | |
| *A01C 21/00* | (2006.01) | |
| *G01N 33/24* | (2006.01) | |

(52) U.S. Cl.
CPC ............ *A01C 7/203* (2013.01); *A01B 63/008* (2013.01); *A01C 5/064* (2013.01); *A01C 21/00* (2013.01); *G01N 33/24* (2013.01); *G01N 2033/245* (2013.01)

(58) Field of Classification Search
CPC ......... A01C 5/062; A01C 5/064; A01C 7/203; A01B 63/008

USPC ............................................. 702/94, 97, 105
See application file for complete search history.

(56) References Cited

U.S. PATENT DOCUMENTS

| | | | |
|---|---|---|---|
| 7,870,826 B2 | 1/2011 | Bourgault | |
| 8,448,717 B2 | 5/2013 | Adams | |
| 8,522,889 B2 | 9/2013 | Adams | |
| 8,550,020 B2 | 10/2013 | Sauder | |
| 9,144,189 B2 | 9/2015 | Stoller | |

(Continued)

FOREIGN PATENT DOCUMENTS

| | | |
|---|---|---|
| DE | 19532870 A1 | 3/1997 |
| DE | 19844395 A1 | 3/2000 |

(Continued)

OTHER PUBLICATIONS

E.T. Weatherly, et al. "Automatic Depth Control of a Seed Planter Based on Soil Drying Front Sensing". 11 pages. vol. 40(2):295-305. 1997 American Society of Agricultural Engineers 0001-2351/97/4002-0295.

(Continued)

*Primary Examiner* — Alicia Torres
(74) *Attorney, Agent, or Firm* — Joseph R. Kelly; Kelly, Holt & Christenson PLLC

(57) ABSTRACT

A planter row unit is positioned so a gauge wheel and an opener are in a known position relative to one another. A planting depth actuator that travels along an extent of travel to change a relationship between the gauge wheel and opener is positioned at one end of its extent of travel, out of engagement with a gauge wheel arm and is then moved to an engagement position where it engages the gauge wheel arm. The location of the engagement position is identified as a calibration point.

20 Claims, 20 Drawing Sheets

(56) References Cited

U.S. PATENT DOCUMENTS

| | | | |
|---|---|---|---|
| 9,307,688 B2 | 4/2016 | Adams et al. | |
| 9,554,504 B2 | 1/2017 | Houck | |
| 9,585,301 B1 | 3/2017 | Lund et al. | |
| 9,723,778 B2 | 8/2017 | Bassett | |
| 10,262,413 B2 | 4/2019 | Strnad et al. | |
| 2004/0211346 A1* | 10/2004 | Beaujot | A01B 63/26 111/170 |
| 2011/0005439 A1* | 1/2011 | Patwardhan | A01C 5/064 111/149 |
| 2013/0112124 A1* | 5/2013 | Bergen | A01C 7/205 111/151 |
| 2015/0296698 A1* | 10/2015 | Schumacher | A01C 7/203 172/4 |
| 2016/0128263 A1 | 5/2016 | Bassett | |
| 2016/0157413 A1* | 6/2016 | Kowalchuk | A01C 7/203 701/50 |
| 2017/0172058 A1 | 6/2017 | Lund et al. | |
| 2017/0367251 A1 | 12/2017 | Hamilton | |

FOREIGN PATENT DOCUMENTS

| | | | |
|---|---|---|---|
| DE | 102016107979 A1 | 11/2016 | |
| FR | 3065146 A1 * | 10/2018 | A01B 63/111 |
| WO | 2012149415 A1 | 11/2012 | |
| WO | 2014066654 A1 | 5/2014 | |
| WO | 2016182906 A1 | 11/2016 | |
| WO | 2017143121 A1 | 8/2017 | |
| WO | 2017143125 A1 | 8/2017 | |

OTHER PUBLICATIONS

Extended European Search Report, Application No. 18200344.2, dated Mar. 13, 2019, 10 pages.

Extended European Search Report, Applicaton No. 18192812.8, dated Mar. 13, 2019, 10 pages.

Extended Europeen Search Report, Application No. 18192555.3, dated Mar. 13, 2019, 10 pages.

U.S. Appl. No. 15/783,271 Office Action dated Apr. 10, 2019, 5 pages.

U.S. Appl. No. 15/783,264 Office Action dated Oct. 5, 2019, 11 pages.

* cited by examiner

CALIBRATING AN ACTUATOR FOR SETTING A SEED DEPTH FOR A ROW UNIT ON A PLANTER

FIELD OF THE DESCRIPTION

The present description relates to agricultural machines. More specifically, the present description relates to setting a planting depth on a planter row unit.

BACKGROUND

There are a wide variety of different types of agricultural machines. Some agricultural machines include planters that have row units. For instance, a row unit is often mounted on a planter with a plurality of other row units. The planter is often towed by a tractor over soil where seed is planted in the soil, using the row units. The row units on the planter follow the ground profile by using a combination of a downforce assembly that imparts a downforce on the row unit to push disc openers into the ground and gauge wheels to set depth of penetration of the disc openers. Some current downforce assemblies provide a relatively fixed downforce. Some allow an operator to change the downforce applied to the row unit by adjusting a mechanical mechanism on the row unit, and others allow the operator to change the downforce from the operator compartment.

In many current systems, the gauge wheels are mounted to the row unit by one or more gauge wheel arms. Setting the seed depth on the planter is done by stopping the planter, exiting the operator compartment and manually adjusting a gauge arm stop to limit movement of the gauge wheel relative to the disc opener. The manual adjustment mechanism often uses a spindle drive, a handle, or another mechanical mechanism that can be used to adjust seed depth. This type of adjustment is somewhat cumbersome and time consuming. It also does not lend itself to frequent changes, because of its cumbersome and time consuming nature.

Therefore, many planting operations are performed with sub-optimal planting seed depth settings. This can result in a loss of yield potential. For instance, at the beginning of a corn planting operation, the operator may set the seed depth to two inches and then leave it at that depth until the corn planting operation is completed. The operator may leave it at this depth even though the depth may be sub-optimal for changing environmental or soil characteristics.

The discussion above is merely provided for general background information and is not intended to be used as an aid in determining the scope of the claimed subject matter.

SUMMARY

A planter row unit is positioned so a gauge wheel and an opener are in a known position relative to one another. A planting depth actuator that travels along an extent of travel to change a relationship between the gauge wheel and opener is positioned at one end of its extent of travel, out of engagement with a gauge wheel arm and is then moved to an engagement position where it engages the gauge wheel arm. The location of the engagement position is identified as a calibration point.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

Figure 1:
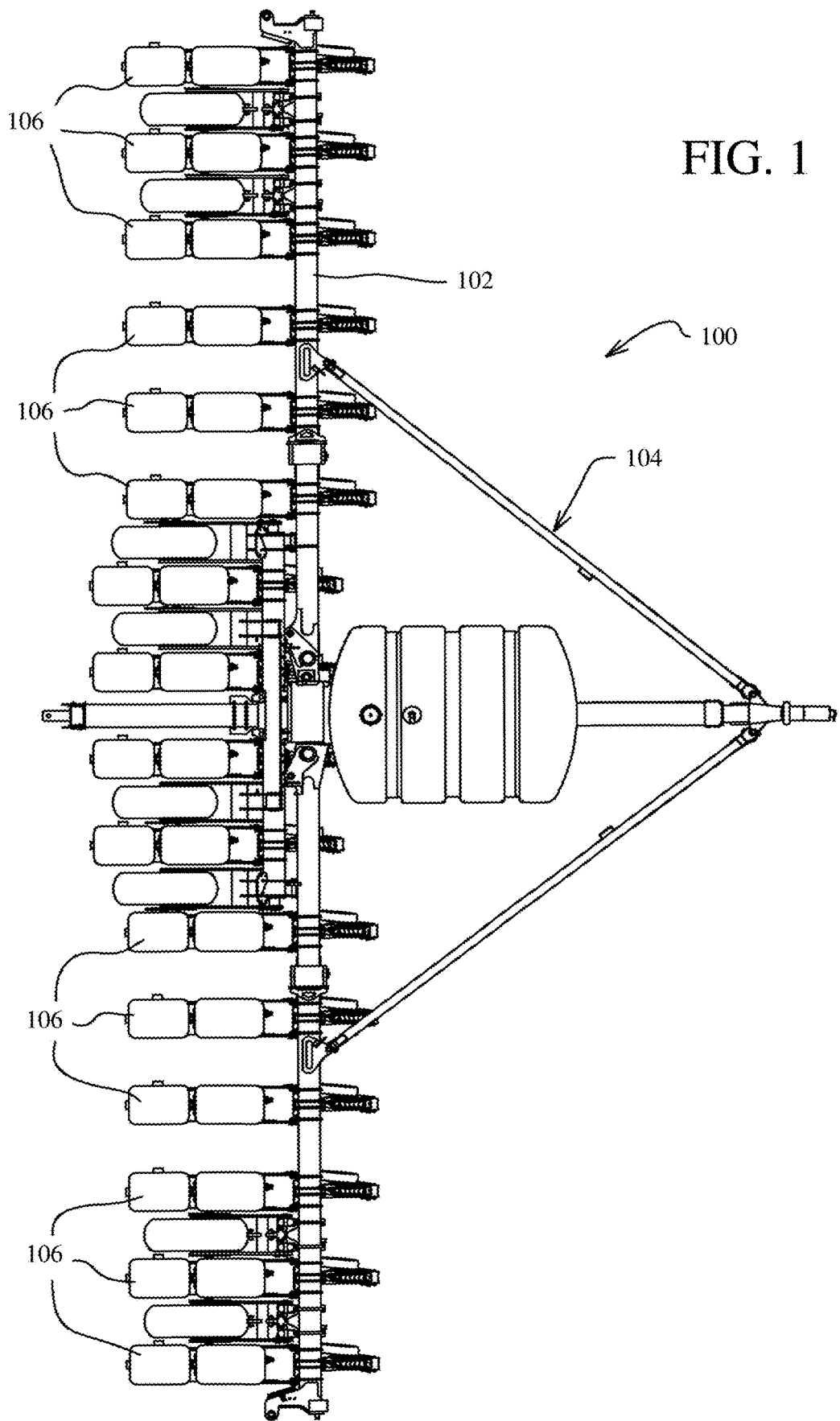
FIG. 1 is a top view of one example of a planting machine.

FIG. 1 is a top view of one example of an agricultural planting machine 100. Machine 100 is a row crop planting machine that illustratively includes a toolbar 102 that is part of a frame 104. FIG. 1 also shows that a plurality of planting row units 106 are mounted to the toolbar 102. Machine 100 can be towed behind another machine, such as a tractor.

Figure 2:
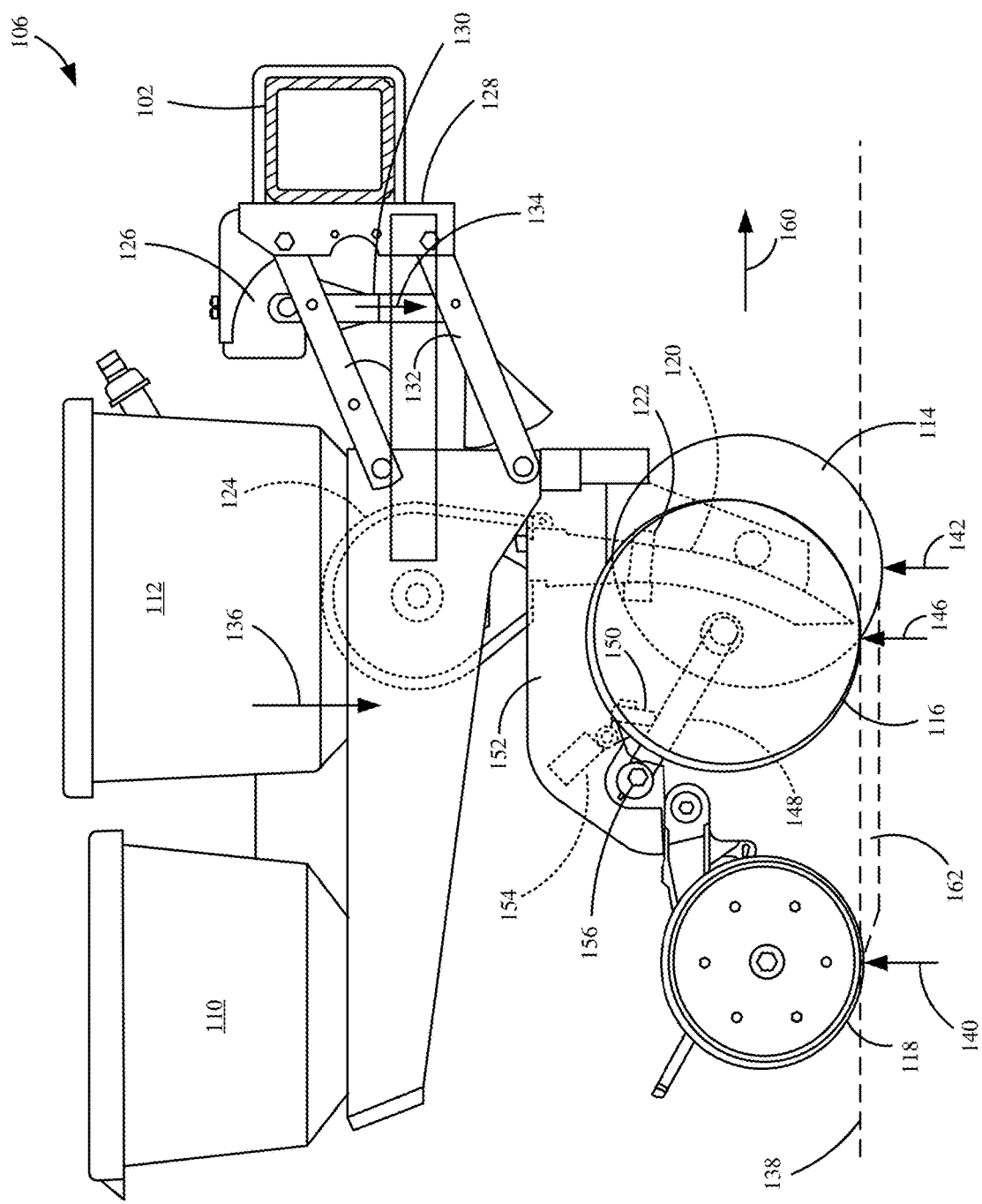
FIG. 2 shows a side view of one example of a row unit of the planting machine illustrated in FIG. 1.

FIG. 2 is a side view showing one example of a row unit 106. Row unit 106 illustratively includes a chemical tank 110 and a seed storage tank 112. It also illustratively includes a disc opener 114, a set of gauge wheels 116, and a set of closing wheels 118. Seeds from tank 112 are fed by gravity into a seed meter 124. The seed meter controls the rate at which seeds are dropped into a seed tube 120 or other seed delivery system, such as a brush belt, from seed storage tank 112. The seeds can be sensed by a seed sensor 122.

It will be noted that there are different types of seed meters, and the one that is shown is shown for the sake of example only. For instance, in one example, each row unit 106 need not have its own seed meter. Instead, metering or other singulation or seed dividing techniques can be performed at a central location, for groups of row units 106. The metering systems can include rotatable discs, rotatable concave or bowl-shaped devices, among others. The seed delivery system can be a gravity drop system (such as that shown in FIG. 2) in which seeds are dropped through the seed tube 120 and fall (via gravitational force) through the seed tube into the seed trench. Other types of seed delivery systems are assistive systems, in that they do not simply rely on gravity to move the seed from the metering system into the ground. Instead, such systems actively capture the seeds from the seed meter and physically move the seeds from the meter to a lower opening, where they exit into the ground or trench.

A downforce actuator 126 is mounted on a coupling assembly 128 that couples row unit 106 to toolbar 102. Actuator 126 can be a hydraulic actuator, a pneumatic actuator, a spring-based mechanical actuator or a wide variety of other actuators. In the example shown in FIG. 2, a rod 130 is coupled to a parallel linkage 132 and is used to exert an additional downforce (in the direction indicated by arrow 134) on row unit 106. The total downforce (which includes the force indicated by arrow 134 exerted by actuator 126, plus the force due to gravity acting on row unit 106, and indicated by arrow 136) is offset by upwardly directed forces acting on closing wheels 118 (from ground 138 and indicated by arrow 140) and double disc opener 114 (again from ground 138 and indicated by arrow 142). The remaining force (the sum of the force vectors indicated by arrows 134 and 136, minus the force indicated by arrows 140 and 142) and the force on any other ground engaging component on the row unit (not shown), is the differential force indicated by arrow 146. The differential force may also be referred to herein as the downforce margin. The force indicated by arrow 146 acts on the gauge wheels 116. This load can be sensed by a gauge wheel load sensor which may be located anywhere on row unit 106 where it can sense that load. It can also be placed where it may not sense the load directly, but a characteristic indicative of that load. Both sensing the load directly or indirectly are contemplated herein and will be referred to as sensing a force characteristic indicative of that load (or force). For example, it can be disposed near a set of gauge wheel control arms (or gauge wheel arm) 148 that movably mount gauge wheels 116 to shank 152 and control an offset between gauge wheels 116 and the discs in double disc opener 114, to control planting depth. Arms (or gauge wheel arms) 148 illustratively abut against a mechanical stop (or arm contact member-or wedge) 150. The position of mechanical stop 150 relative to shank 152 can be set by a planting depth actuator assembly 154. Control arms 148 illustratively pivot around pivot point 156 so that, as planting depth actuator assembly 154 actuates to change the position of mechanical stop 150, the relative position of gauge wheels 116, relative to the double disc opener 114, changes, to change the depth at which seeds are planted. This is described in greater detail below.

In operation, row unit 106 travels generally in the direction indicated by arrow 160. The double disc opener 114 opens a furrow in the soil 138, and the depth of the furrow 162 is set by planting depth actuator assembly 154, which, itself, controls the offset between the lowest parts of gauge wheels 116 and disc opener 114. Seeds are dropped through seed tube 120, into the furrow 162 and closing wheels 118 close the soil.

In prior systems, in order to change the planting depth, the operator of the towing vehicle would dismount the towing vehicle and operate a mechanical actuator that would adjust the position of mechanical stop 150. This would be done on each row unit. In accordance with one example, actuator assembly 154 can be automatically actuated by a control system, from the operator compartment of the towing vehicle. It can be actuated based on an operator input detected through that control system, or it can be automatically actuated to automatically change the planting depth as row unit 106 is towed across the field. In one example, and as is described in greater detail below, it can be actuated to maintain a desired trench contour or trench profile so that the depth of the seed trench varies, in a desired way.

Figure 3:
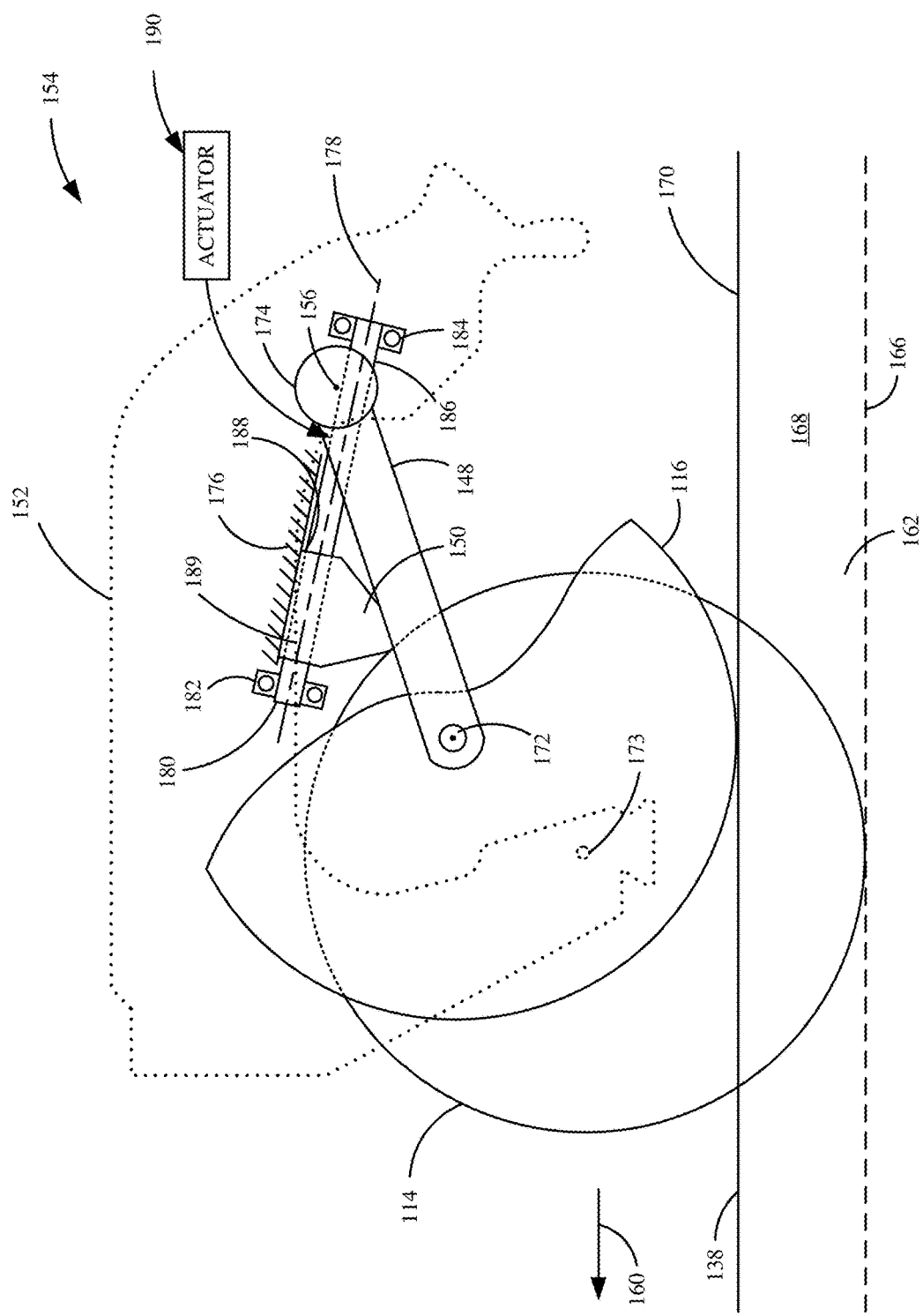
FIG. 3 shows one example of a planting depth actuator assembly.

FIG. 3 shows one example of the planting depth actuator assembly 154, in more detail. Planting depth actuator assembly 154 illustratively includes an actuator 190 that drives rotation of a linkage that, itself, drives movement of mechanical stop 150. In one example, the linkage can include a drive mechanism 180 which can be coupled to output of action 190. Drive mechanism 180, in turn, drives movement of a mechanical stop or wedge 150, as is described in more detail below. Because FIG. 3 is a side view, only one opening disc 114, gauge wheel 116, closing disc 118 and gauge wheel arm 148 are shown. It will be appreciated, however, that each of these can have another member to form a pair. This is one example only. Similar items to those shown in FIG. 2 are similarly numbered.

FIG. 3 shows that the disc opener disc 114 are rotatably mounted to shank 152 at point 173. are pulled through the soil in the direction indicated by arrow 160 and they open a trench or furrow 162 in the soil. The seeds are placed into trench (or furrow)162. The trench is defined by a bottom soil portion 166, trench sidewalls (one of which is shown at 168) and the soil surface 170. The vertical distance between the soil surface 170 and the trench bottom 166 is defined as the planting depth. To obtain a desired planting depth, the pair of gauge wheels 116 are forced into contact with, and follow, the soil surface 170. A downforce system (such as downforce actuator 126 and parallel linage 132 shown in FIG. 2) is used to apply a downforce on row unit 106 to ensure full penetration of the opener discs resulting in ground contact between the gauge wheels 116 and the soil surface 170 with the gauge wheels arm 148 engaging the stop 150.

Gauge wheels 116 are movably connected to the row unit shank 152 by a set of gauge wheel arms 148. The gauge wheels 116 are each connected to an arm 148 by a rotary joint 172. Similarly, each arm 148 is connected to shank 152 by rotary joint 174, so that they are pivotable about a pivot point 156. As the arms 148 pivot about pivot point 156, they move upwardly and downwardly in FIG. 3 to increase or decrease, respectively, the distance between the bottom most points of opening discs 114 and gauge wheels 116, and thus change the planting depth (the depth of a furrow 162).

In the example shown in FIG. 3, the mechanical stop 150 is formed by a wedge that is located between the gauge wheel arm 148 and a further mechanical stop 176 that may be defined by a portion of the row unit shank 152. The position of the wedge is illustratively changed along a longitudinal axis 178 of a drive mechanism 180. As the position of the wedge 150 is changed along axis 178, it changes the position of the upper limit of rotation of gauge wheel arm 148 about pivot point 156. Thus, when the gauge wheel 116 is forced into contact with the ground, wedge 150 defines the position of gauge wheels 116 relative to the row unit shank 152 and relative to opening discs 114, thus defining planting depth.

In one example, drive mechanism 180 is a lead screw that is mounted inside the row unit shank 152 using a set of bearings 182 and 184. The lead screw illustratively has a threaded exterior surface 186 that interacts with a threaded interior surface 188 of a carriage 189 that carries wedge 150 so that, as lead screw 180 rotates within bearings 182 and 184, it drives movement of wedge 150 along longitudinal axis 178 in a direction that is determined by the direction of rotation of lead screw 180. Changing the position of wedge 150 along axis 178 thus changes the angle between the longitudinal axis 178 of lead screw 180 and the elongate axis of gauge wheel arms 148.

In one example, actuator 190 drives rotation of lead screw 180 at a controllable speed and in a controllable direction. Actuator 190 may illustratively be an electric motor with a locking member (such as a self-locking worm drive) mounted between the electric motor and lead screw 180. This can serve to increase the torque available to turn lead screw 180. The self-locking characteristic of the worm drive allows the worm drive to hold the set depth while downforce is acting on gauge wheels 116, without torque being applied to the electric motor or other actuator 190. This also illustratively allows the position of wedge 150 to be changed while downforce is acting on the gauge wheel 116, and allows the actuator 190 to overcome frictional forces between wedge 150 and gauge wheel arms 148, as well as those forces between wedge 150 and mechanical stop 176, and further frictional forces between the interior threaded surface 188 of carriage 189 and the exterior threaded surface 186 of lead screw 180. A different gear ratio may be used, depending upon the force available from actuator 190. In one example, the gear ratio may be 1:20, although this is just one example.

Figure 4:
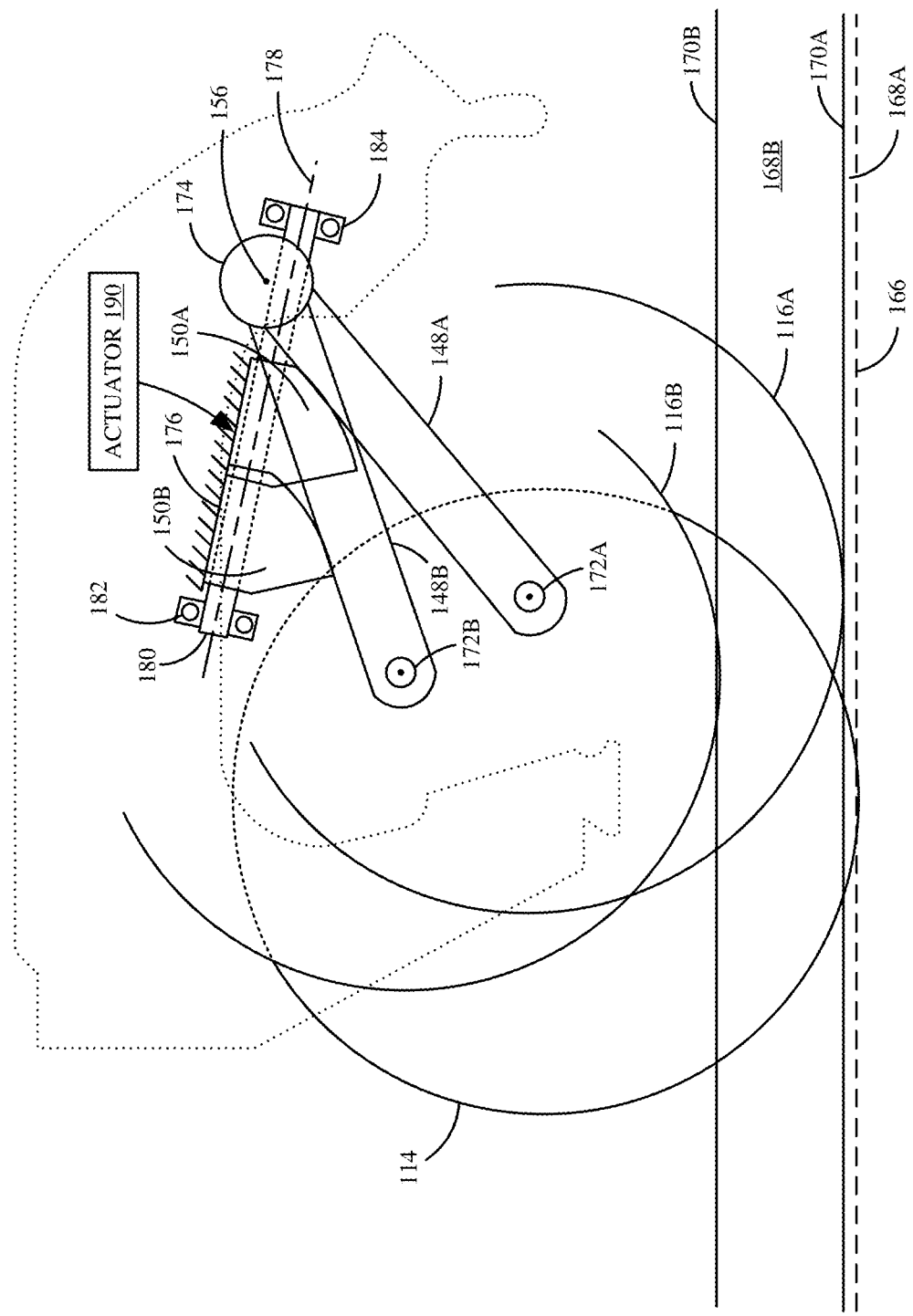
FIG. 4 shows the actuator assembly illustrated in FIG. 3, in two different positions.

FIG. 4 shows gauge wheels 116 in two different positions relative to disc opener 114. The items in FIG. 4 are similar to those shown in FIG. 3, and they are similarly numbered. However, when the items, are at a first planting depth setting, the items are labeled "A" and when in a second depth setting, they are labeled "B". In position B, it can be seen that the planting depth is deeper. This is because wedge 150 is moved along axis 178 more toward bearing 182 so that gauge wheel arm 148B is rotated vertically upward about point 156 more than in position A. Thus, the distance between the lower most point of disc opener 114 and gauge wheel 116B is relatively large. In position A, wedge 150 is moved along axis 178 more toward bearing 184 so that gauge wheel arm 148A is rotated further downwardly about point 156. Thus, the lower most point of disc opener 114 and that of gauge wheel 116A are relatively close to one another. Thus, in position B, the trench 168B is relatively deep while in position A, the trench 168A is relatively shallow.

It should be noted that different configurations of wedge 150 are contemplated herein. For instance, in one example, wedge 150 may illustratively be configured as a single piece that engages both of the left and right gauge wheel arms 148 (both the arm 148 shown in FIG. 4 and the other gauge wheel arm which is not shown in the figures, and which corresponds to the other gauge wheel, also not shown in the figures). However, the wedge is illustratively configured as a rocker so that it can rotate slightly about axis 178. This rocker configuration is used to allow some independent motion of the left and right gauge wheels 148 relative to one another. This may occur, for instance, when the row unit 106 is traveling over uneven terrain.

In another example, however, wedge 150 may have no direct contact with the gauge wheel arms 148. Instead, a separate rocker mechanism can be interposed between wedge 150 and the corresponding set of gauge wheel arms 148. In still another example, a separate wedge can interact with each separate gauge wheel arm 148. These and other configurations are contemplated herein.

It will also be noted that, in one example, wedge 150 can also include a downforce sensor. The downforce sensor may be a load cell or another sensing device to determine the downforce between the corresponding gauge wheels 148 and the ground (e.g., the downforce margin).

In another example, wedge 150 or carriage 189 can incorporate a scraper, a rubber lip, or other mechanisms that can be used to clean the lead screw 180 of debris. It can also include a set of plastic bristles or other cleaner.

In yet another example, the gauge wheel arms 148 may illustratively be curved. This can be done so that the position where force is induced on the rocker or wedge 150 and/or the direction and magnitude of the applied force on the rocker or wedge 150 is substantially equal for all depth settings. It will be appreciated that, instead of curving arms 148, the surface of wedge 150 or a corresponding rocker may be curved as well, or both the wedge 150 and arms 148 can be curved.

Figure 5:
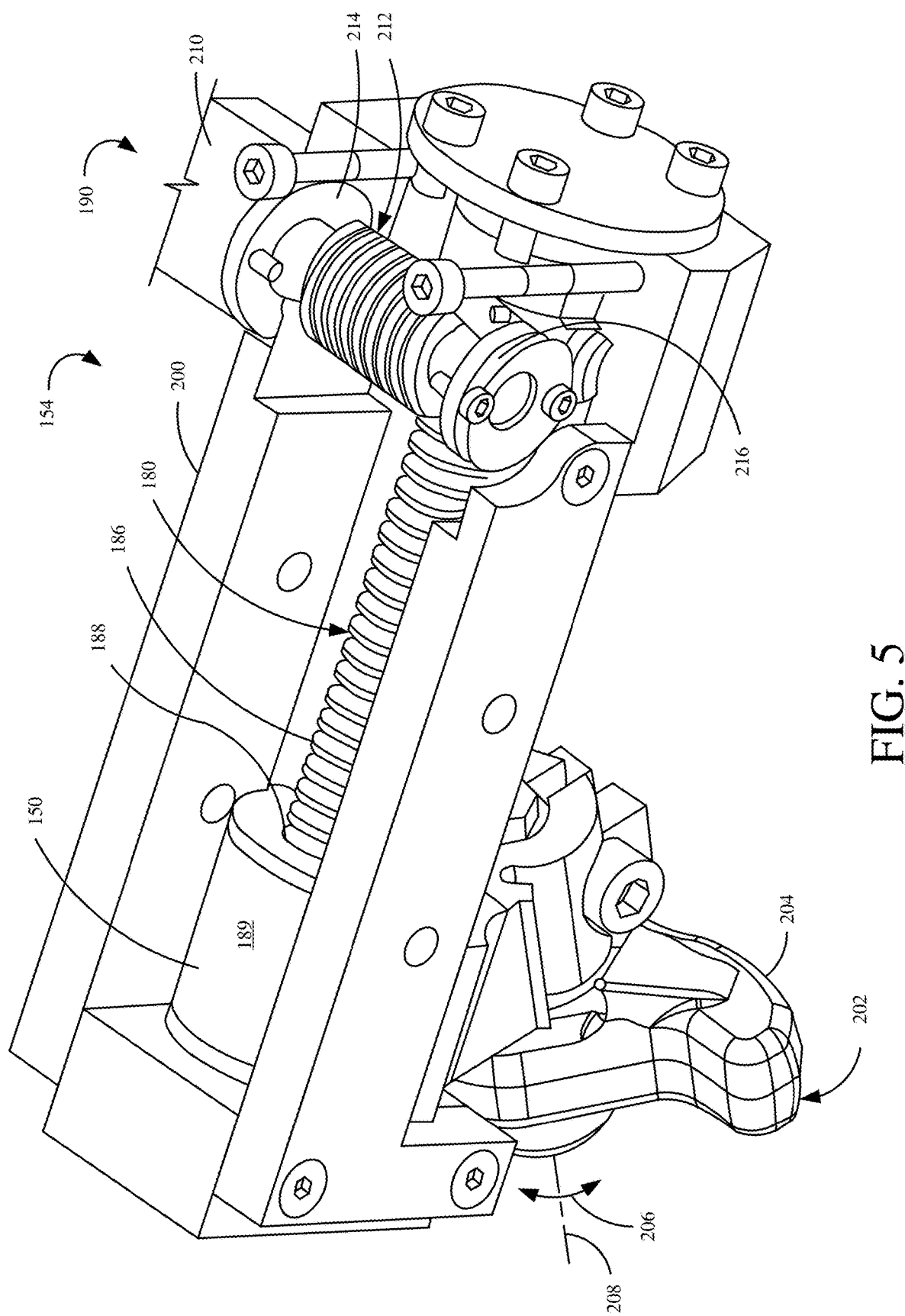
FIG. 5 is a perspective view of one example of a portion of the actuator assembly illustrated in FIGS. 3 and 4.

FIG. 5 is a perspective view of one example of the planting depth actuator assembly 154, in more detail. Some of the items are similar to those shown in FIG. 3 above, and they are similarly numbered. FIG. 5 shows that, in one example, a frame structure 200 supports lead screw 180 and bearings 182 and 184 in, or attached to, shank 152 (not specifically shown in FIG. 5). The wedge 150 has carriage 189 with the threaded interior surface 188 that travels over the threaded exterior surface 186 of lead screw 180. FIG. 5 also shows that the lower portion of wedge 150 is formed as a rocker 202. Rocker 202 may illustratively include a first arm engaging portion 204 that engages gauge wheel arm 148 and second arm engaging portion (not shown) that engages the second gauge wheel arm 148 (also not shown). It rocks generally in the directions indicated by arrow 206 about an axis 208 of a mechanical assembly that fastens rocker 202 to the wedge 150 so that it moves with wedge 150 as wedge 150 travels along lead screw 180. The rocking movement about axis 208 accommodates some independent movement of the gauge wheel arms.

FIG. 5 also shows one example of an actuator 190 which includes motor 210 that drives rotation of a self-locking worm drive 212 which rotates within a set of bushings 214 and 216. Motor 210 illustratively drives rotation of the worm portion of worm drive 212. Rotation of the worm portion is illustratively translated into rotational movement of lead screw 180 through a worm gear (not shown) in a self-locking way. Worm drive 212 thus acts as a locking member that locks wedge 150 in place. Therefore, any torque or other forces imparted to the rocker mechanism or the wedge 150 are not fed back to the drive output of motor 210. Instead, they are transmitted back to shank 152 through frame structure 200.

Figure 6:
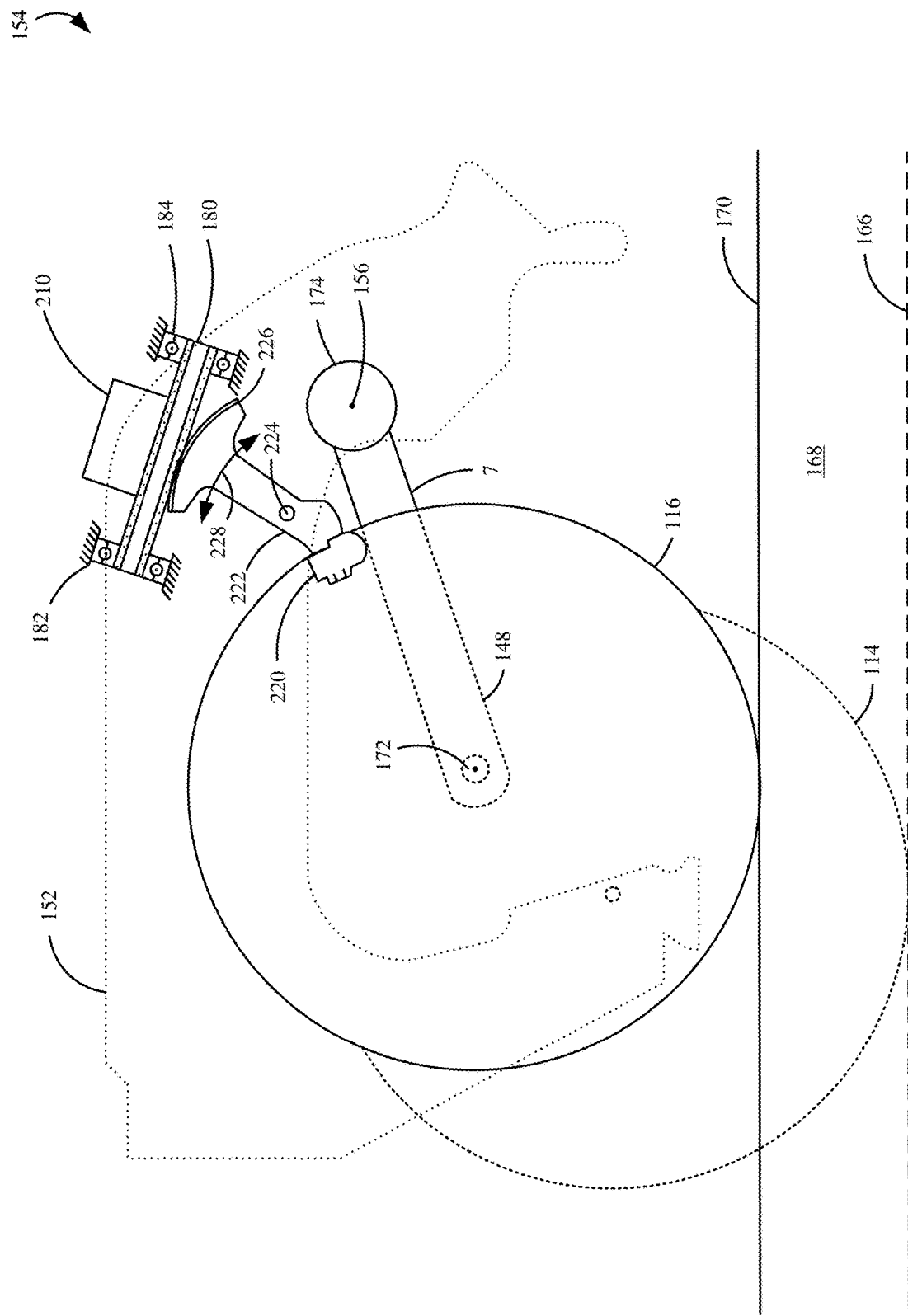
FIG. 6 illustrates another example of a planting depth actuator assembly.

FIG. 6 shows another example of a planting depth actuator assembly 154 that can be used to automatically set the planting depth of a row unit 106. Some items are similar to those shown in previous figures, and they are similarly numbered. In the example shown in FIG. 6, a rocker 220 (or other gauge wheel arm contact member or abutment member) is carried by an adjustment lever 222 that rotates relative to shank 152 about axis of rotation 224. As it rotates about axis 224, it drives member 220 to impart force on, and rotate, gauge wheel arm 148 downward about pivot point 156, or it allows gauge wheel arm 148 to move upward about pivot point 156. Adjustment arm 222 illustratively has a gear wheel portion 225 that interacts with the threaded surface of lead screw 180. As lead screw 180 rotates, it thus drives movement of the gear wheel portion 226 to, correspondingly, drive rotation of arm 222 about axis 224 in the directions indicated by arrow 228. By choosing the geometry of the adjustment arm 222 and the gear wheel portion 226, the point at which force is applied from abutment member 220 to arm 148 can be adjusted. In one example, it can be adjusted so the point at which member 220 applies force to arm 148 is the same, regardless of the planting depth. Also, by choosing the geometry of adjustment arm 222, the force needed to rotate lead screw 180, in order to drive movement of member 220, can be adjusted as well.

In the example illustrated, lead screw 180 may instead be a self-locking worm drive which is connected to electric motor 210 by a worm gear. A reduction gear unit can be implemented to deliver desired torque. The position of the adjustment arm 222 can thus, in one example, only be changed by motor 210 to actively drive the worm of the worm drive 180 because of the self-locking nature of the worm gear. When the motor is not actively driving the worm portion of worm drive 180, then any forces that are occurring on the worm drive 180 are transmitted from there to the mounting points of bearings 182 and 184, and finally to shank 152. This allows isolation of any impact forces that may impact gauge wheel 116, and thus gauge wheel arm 148, from the electric motor 210 and thereby protects electric motor 210 from peak loads.

Figure 7:
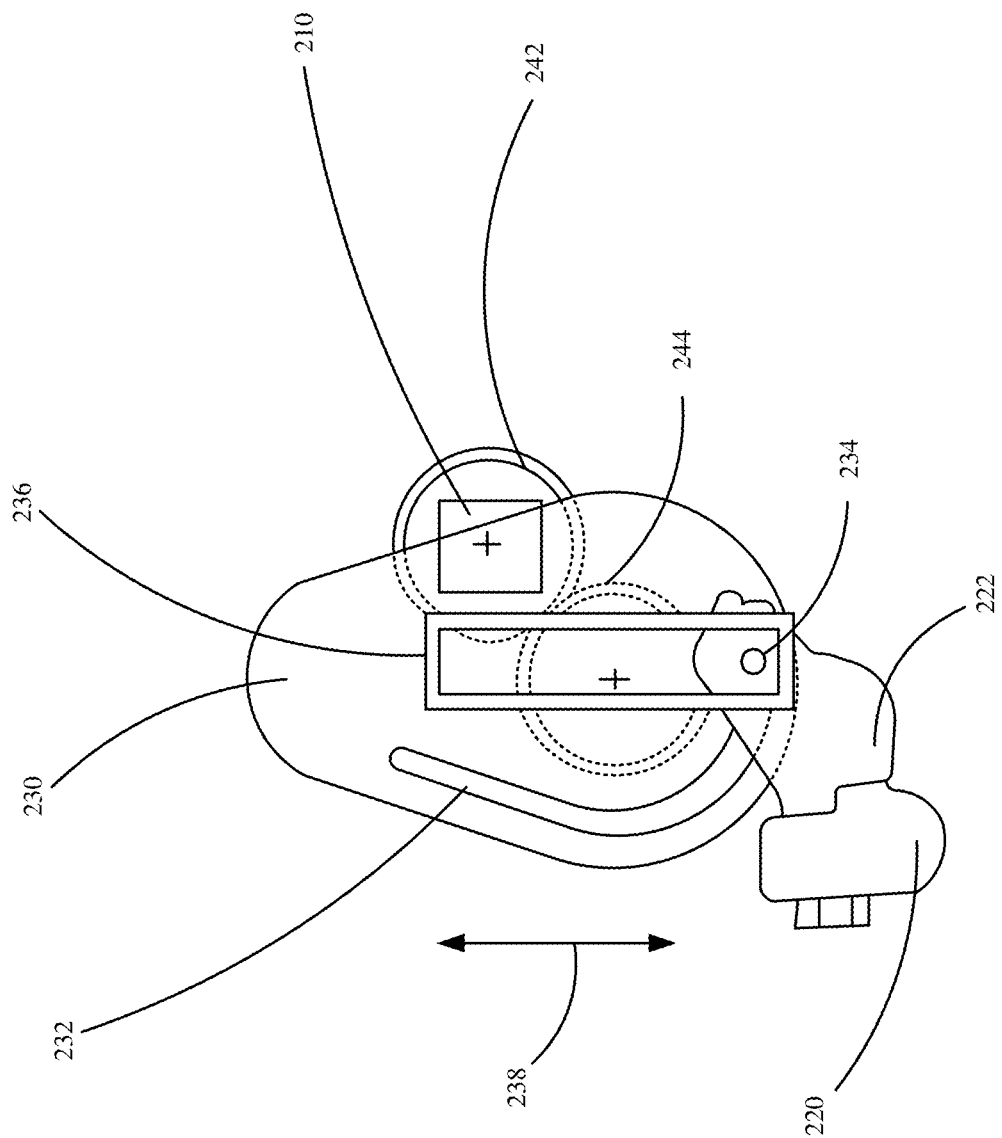
FIG. 7 illustrates another example of a planting depth actuator assembly.

FIG. 7 shows another example of a planting depth actuator assembly 154. Some items are similar to those shown in FIG. 6, and they are similarly numbered. In the example shown in FIG. 7, the upper limitation of movement of gauge wheel arm 148 is controlled by rotation of cam 230. The cam defines a groove 232 to guide the movement of a support arm 222 and abutment member (or rocker) 220. As cam 230 is rotated, a mounting pin 234 follows groove 232. Because pin 234 resides in and follows groove 232, an upward bearing is provided in situations where the planter or row unit 106 is lifted and the gauge wheel 116 and arm 148 do not press abutment member 220 against the cam 230. A second groove defined by groove defining member 236 guides movement of arm 222 and abutment member 220 in a direction generally indicated by arrow 238. Thus, as cam 230 is driven by an actuator (such as an electric motor), pin 234 follows groove 232 but it also follows the groove defined by frame structure 236. Therefore, as cam 230 is driven, this drives vertical movement (in the direction indicated by arrow 238) of abutment member 220. Because abutment member 220 bears against the gauge wheel arm(s) 148, it thus causes rotation of the gauge wheel arms 148 about their pivot points 156 (as shown with respect to the above figures).

In the example shown in FIG. 7, it can be seen that any vertical force(s) resulting from the gravitational force of the row unit 106 and any additional applied downforce, less the resistance of the soil to reach the desired depth, is born solely by cam 230. The actuation of the cam can be implemented either directly by integrated teeth partially on the shorter part of the cam or the cam can be connected to a drive shaft on which a gear, such as gear 242, is mounted. A relatively low speed and a relatively high torque is then applied to the cam 230 in order to control the corresponding planting depth. In another example, a gear box 244, (or gear reduction) between cam 230 and gear 242 (which is driven by motor 210) can be provided. Gear box 244 can have a relatively high transmission ratio in order to supply torque as well as precise control of the depth. A worm drive can be used for the same reasons as described above (e.g., a high transmission ratio and self-locking features). A planetary gear box or other types of gear boxes can be used as well.

Figure 8:
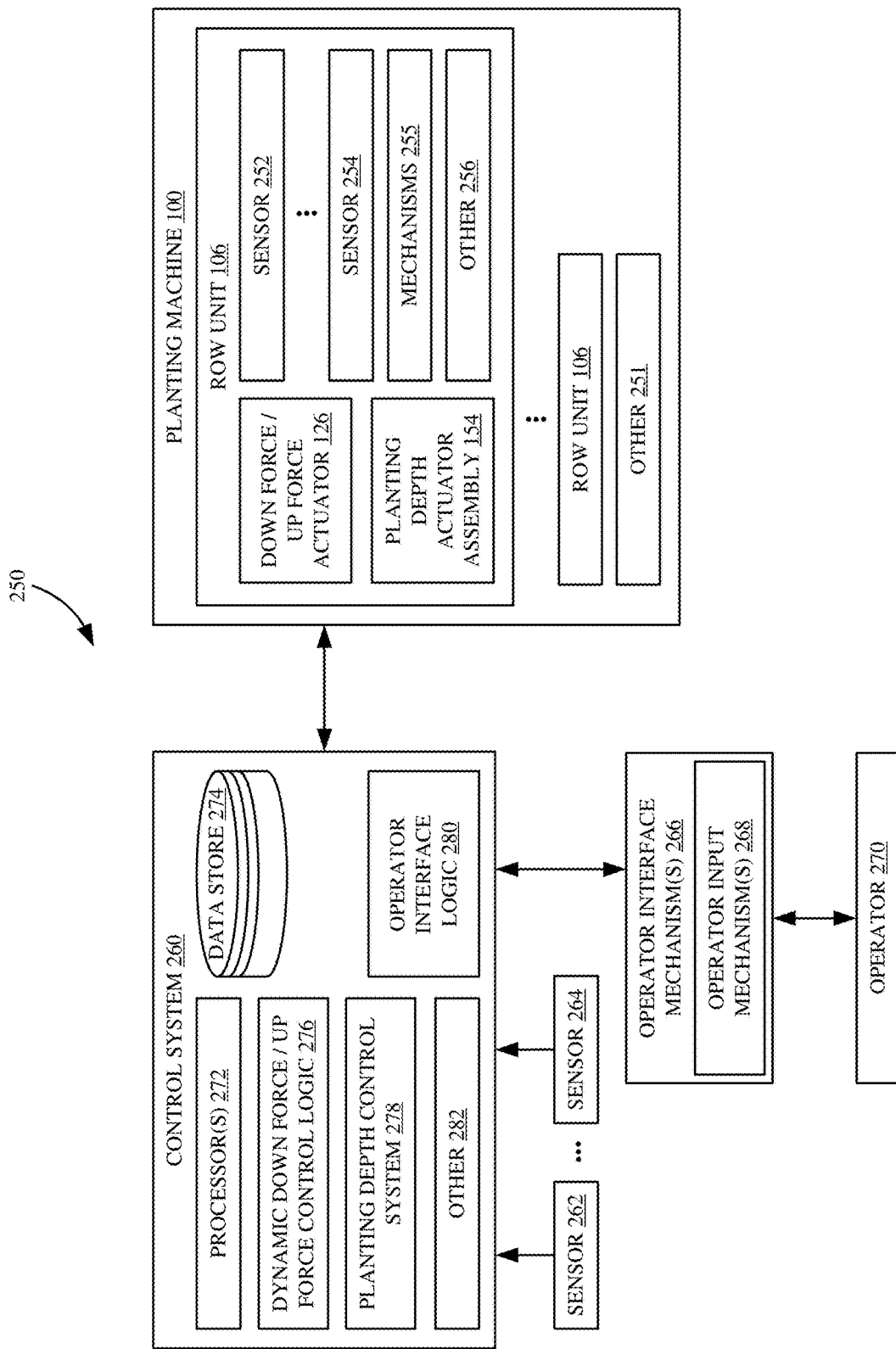
FIG. 8 is a block diagram showing one example of a planting machine architecture.

FIG. 8 is a block diagram of one example of a planting machine architecture 250 for automatically controlling planting depth. Architecture 250, includes a planting machine, such as planter 100 (also shown in FIG. 1) which has a plurality of row units (such as row units 106 also shown in FIG. 1) and it can have other items 251. Each row unit may have one or more sensors 252-254. Row unit 106 is also shown with other mechanisms 255. Mechanisms 255 illustratively include gauge wheels 116, disc opener 114, closing wheels 118, and some or all of the other mechanisms shown in previous figures on row unit 106 or different mechanisms.

Row unit 106 can have a wide variety of other things 256 as well.

Also, as shown in FIG. 8, each row unit 106 may have the downforce actuator 126 and a planting depth actuator assembly 154. In some examples, downforce actuator 126 illustratively exerts additional downforce on row unit 106 to keep gauge wheels 116 in contact with the ground, as discussed above with respect to FIG. 2. Also, in one example, downforce actuator 126 may also be an upforce actuator which can be used to lift the gauge wheels 116, relative to the disc opener 114. In examples where downforce actuator 126 is also an upforce actuator that can exert upward force on the gauge wheels 116, then planting depth actuator assembly 154 may not be needed. These and other examples are described in more detail below.

Planting depth actuator assembly 154, as discussed above, illustratively controls the distance between the lower most points of the gauge wheels 116 and disc opener 114. Therefore, it can be actuated to control the planting depth at which row unit 106 plants seeds. Sensors 252-254 can be any of a wide variety of sensors. For instance, in one example, sensor 252-254 include a downforce sensor that senses the downforce exerted by downforce actuator 126 on row unit 106. In another example, they can be a combination of sensors and logic that senses a downforce margin, as described above. Sensors 252-254 may illustratively include a position sensor that senses the position of gauge wheels 116 relative to disc opener 114. It can be a sensor that senses the depth of the seed trench. The sensors can include a wide variety of other sensors as well, such as sensors that sense soil characteristics (such as moisture, soil compactness, soil type, etc.), and environmental characteristics. The sensors can sense a wide variety of other variables (machine variables, soil variables, environmental variables, etc.) as well.

FIG. 8 also shows that, in one example, control system 260 can illustratively receive inputs from additional sensors 262-264, and it can also interact with operator interface mechanisms 266. Operator interface mechanisms 266 can include operator input mechanisms 268 that operator 270 can interact with in order to control and manipulate control system 260, and some parts of planting machine 100.

Therefore, in the example illustrated, control system 260 can include one or more processors 272, a data store 274, dynamic downforce/upforce control logic 276, planting depth control system 278, operator interface logic 280, and it can include a wide variety of other items 282. Dynamic downforce/upforce control logic 276 is included in scenarios where downforce/upforce actuator 126 can be dynamically controlled by operator 270, from the operator compartment of the tractor or other towing vehicle, to controllably impart a either downforce on row unit 106, an upforce, or both.

Planting depth control system 278 illustratively receives sensor inputs and/or operator inputs. It controls planting depth actuator assembly 154, on each row unit 106, in order to control the planting depth used by the row units 106 on planting machine 100.

Operator interface mechanisms 266 can include a wide variety of mechanisms, such as a display screen or other visual output mechanisms, audio mechanisms, haptic mechanisms, levers, linkages, buttons, user actuatable display elements (such as icons, displayed links, buttons, etc.), foot pedals, joysticks, steering wheels, among a wide variety of others. Operator interface logic 280 illustratively controls outputs on the operator interface mechanisms 266 and can detect operator inputs through the operator input mechanisms 268. It can communicate an indication of those inputs to other items in control system 260 or elsewhere.

Sensors 262-264 can also be a wide variety of different types of sensors that can be used by dynamic downforce/upforce control logic 276, planting depth control system 278, or other items. Some of these are described in greater detail below.

FIG. 8 shows that, in one example, architecture 250 includes a planting machine (such as planting machine 100 shown in the previous figures) and a control system 260. Control system 260 can be carried by the towing machine that is towing planting machine 100, it can be carried by planting machine 100, or it can be distributed among the towing machine, planting machine 100 and a wide variety of other locations. In one example, control system 260 generates control signals to control the planting machine 100, and as will be described in greater detail more specifically below, the planting depth that the row units on planting machine 100 are using to plant seeds. FIG. 8 also shows that, in one example, control system 260 can receive sensor signals from a plurality of different sensors 262 and 264. It also shows that operator 270 (which may be the operator of the towing vehicle) can interact with control system 260 through operator interface mechanisms 266 which can include, for instance, operator input mechanisms 268.

Figure 9:
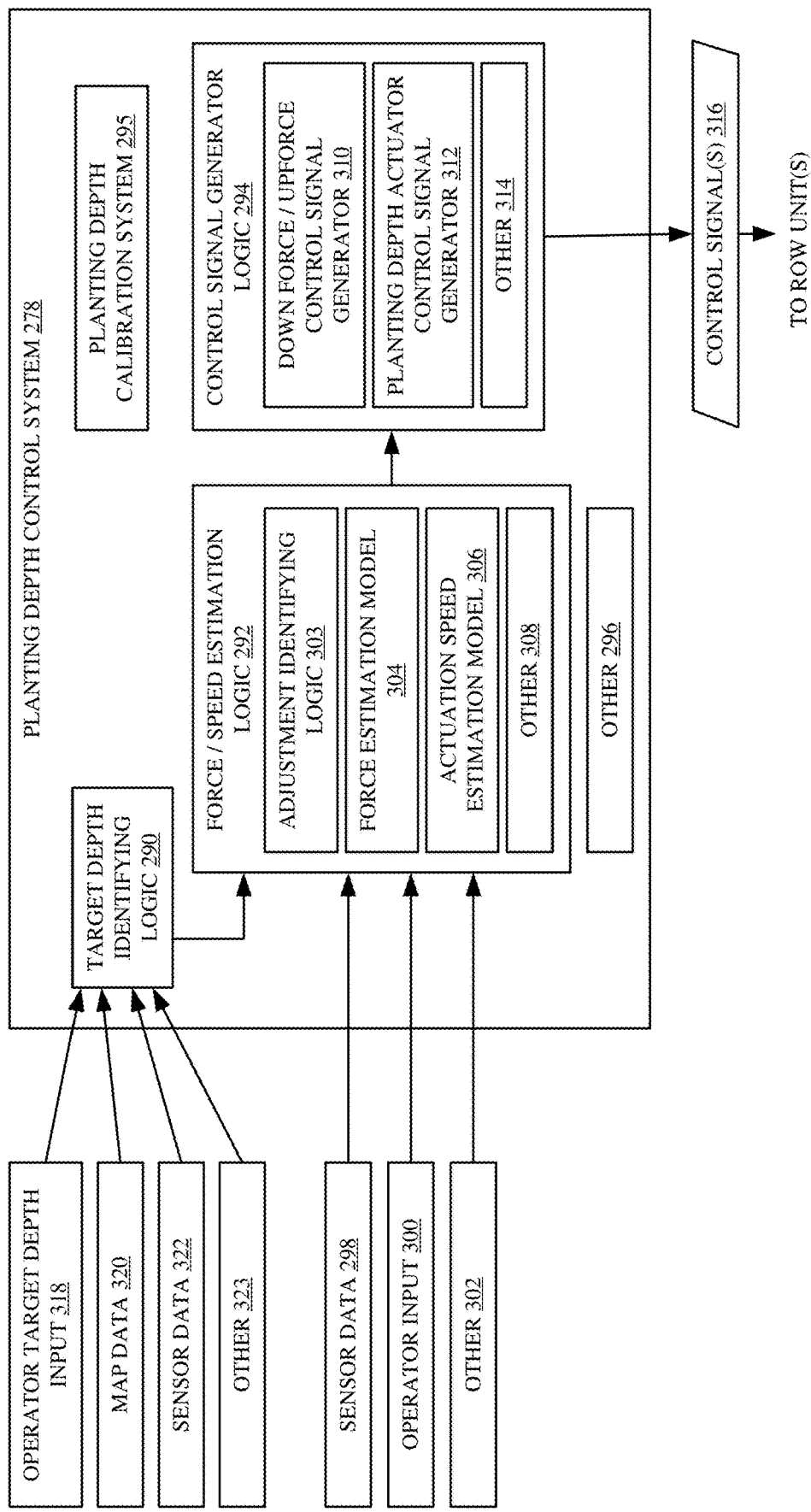
FIG. 9 is a block diagram showing one example of a planting depth control system in more detail.

FIG. 9 shows one example of planting depth control system 278 in more detail. In the example shown in FIG. 9, planting depth control system 278 can include target depth identifying logic 290, force/speed estimation logic 292, control signal generator logic 294, planting depth calibration system 295, and it can include a wide variety of other items 296. Force/speed estimation logic 292 illustratively receives a target depth which identifies a desired planting depth for planting machine 100. It can also identify individual planting depths for individual row units 106 on planting machine 100. It can receive the target depth from target depth identifying logic 290, from an operator or from another source.

Target depth identifying logic 290 can identify the target depth in a variety of different ways. For instance, it can receive an operator target depth input 318 that identifies a target depth input by the operator 270. It can include map data 320 which includes a wide variety of different information correlated to different geographic locations within the field that is being planted. The information can include soil moisture information, soil type information, soil compactness information and a wide variety of other information that can be used by target depth identifying logic 290 to identify a desired target depth. Logic 290 can also receive sensor data 322 which is indicative of one or more variables that may have an effect on the identified target planting depth. Again, for instance, sensor data 322 can be data generated from a soil moisture sensor, a soil type sensor, a soil or environmental characteristic sensor that senses other soil characteristics (such as compaction or other characteristics) or other environmental characteristics, such as topology, position, etc. Sensor data can include data generated by machine sensors that sense machine variables or other items.

As planting machine 100 moves about the field, it may be that the target planting depth identified by target depth identifying logic 290 changes based on the location of planting machine 100. Therefore, logic 290 may receive a location sensor input indicative of that location, and other inputs that bear on the desired target planting depth, and it may modify the target planting depth as machine 100 moves about the field. Thus, the target planting depth provided by logic 290 to force/speed estimation logic 292 may vary. All of these and other scenarios are contemplated herein.

Force/speed estimation logic 292 is also shown receiving, by way of example, sensor data 298, one or more operator inputs 300, and it can include a wide variety of other inputs 302. It illustratively generates an estimate of the force and speed that will be needed to control planting depth actuator assembly 154 in order to achieve the target planting depth. Thus, it can include force estimation model 304 that is used to estimate the force that will be needed to achieve the target planting depth. It can also illustratively include actuation speed estimation model 306 that generates an estimate of the speed at which planting depth actuator assembly 154 is to be actuated to move from a current planting depth to the target planting depth. It can include other items 308 as well. By way of example, force estimation model 304 may estimate a force that needs to be applied to the gauge wheel arms 148 in order to move the gauge wheel in the desired direction (either up or down relative to the disc opener 114). Actuation speed estimation model 306 illustratively generates an estimate indicative of how quickly actuator assembly 154 should be actuated to move the gauge wheels to the desired target depth. For instance, it may be that it is undesirable to change the depth profile of the seed trench too quickly. Instead, it may be that it is desired to change planting depth gradually to achieve a desired trench contour or trench depth profile. Thus, actuation speed estimation model 306 can generate an estimate indicating how quickly the actuator assembly 154 should be actuated to change the planting depth.

In one example, the force estimation and speed estimation are provided to control signal generator logic 294 which illustratively includes downforce/upforce control signal generator 310, planting depth actuator control signal generator 312, and it can include other items 314. In some examples, control signal generator 310 will control the downforce/upforce actuator 126 (shown in FIG. 8) to remove any applied downforce or to supply an upforce so that the planting depth actuator assembly 154 need not overcome any applied downforce in changing the planting depth. Control signal generator 312 then illustratively controls the planting depth actuator assembly 154 to change the planting depth at a speed corresponding to the speed estimated by model 306. The output of control signal generator logic 294 is illustratively a set of control signals 316 that are output to row units 106 in order to control downforce/upforce actuator 126 and/or planting depth actuator assembly 154.

As mentioned above, one parameter associated with planting is the depth below the surface of the soil that seed is planted. Various methods have been shown for sensing the depth at which a seed is being placed, while planting. The planting depth (along with other variables, such as soil texture, temperature, moisture, etc.) can effect emergence time and plant vigor. Generally, yield is optimized by having all plants emerge as evenly as possible, but there may be conditions in which it is best to stagger emergence or plant maturity. In addition, the emergence may differ, from one piece of ground to another, if planting depth is maintained constant. Therefore, varying plating depth may be used to obtain uniform emergence as well.

While the row unit is engaging the ground and planting, the forces needed to change the planting depth on-the-go, can be significant. Actuators that are large enough and strong enough to operate against such forces can be relatively large and costly. One way of changing planting depth, as is described below, may involve stopping the planting machine, lifting the row units out of the ground, and then automatically actuating the actuator assembly 154 to change the planting depth automatically, before continuing. This may happen at the end rows or it may occur during a brief pause of forward motion to raise the machine while planting to facilitate such an adjustment. The actuators needed to change planting depth can then be relatively small because they need not overcome the large downforces involved with some types of planting equipment.

In another example that is described in more detail below, the downforce/upforce control signal generator 310 controls the downforce/upforce actuator 126 in conjunction with the planting depth actuator control signal generator 312 controlling the planting depth actuator assembly 154, to change planting depth. Control signal generator 310 can control downforce actuator 126 to momentarily relieve any applied downforce, and to optionally provide the force needed to either raise (upforce) or further lower (downforce) one or more row units 106 into the ground with respect to where the gauge wheels 116 are riding at the soil surface. Control signal generator 312 can then control planting depth actuator assembly 154 to simply lock in the new desired depth. This reduces the need of assembly 154 to be able to exert the extra force (and thus incur the extra cost and extra structural stress) that is needed to overcome the downforce, while still allowing the row unit 106 to adjust planting depth on-the-go. Thus, it can be seen that in one example, the downforce/upforce control signal generator 310 can be used to provide all of the power needed to change the planting depth, in which case planting depth actuator control signal generator 312 controls planting depth actuator assembly 154 to simply lock in the new depth. In another example, the downforce/upforce control signal generator 310 can generate a portion of the needed force to adjust the relationship between gauge wheels 116 and opener 114, or it can simply be used to remove any dynamically applied downforce so the planting depth can be made using a smaller actuator. In these latter two scenarios, the planting depth actuator assembly 154 includes an actuator in addition to actuator 126 which provides additional planting depth adjustment force to change the relationship between gauge wheels 116 and disc opener 114, and to make the planting depth adjustment, and then to lock that adjustment in place.

Also, it will be noted that, in one example, planting depth control system 278 controls planting depth using a control curve that plots desired planting depth against the position of the mechanical stop 150 on the planting depth actuator assembly 154. Calibration of the control curve may be used to accommodate for changes in the relationship between the planting depth and the position of mechanical stop. For instance, as the opener 114 and gauge wheels 116 are used, they can wear at different rates. Manufacturing and assembly tolerances can also lead to changes. Therefore, as discussed in greater detail below with respect to FIGS. 11-13, calibration system 295 can calibrate the control curve.

Before describing the operation of planting depth control system 278 in more detail, a number of things will first be noted. When the planting depth of a row unit is changed, it can be changed either from a shallower depth to a deeper depth, or from a deeper depth to a shallower depth. When the planting depth is changed within a field, as the planting machine 100 is moving and planting (e.g., when it is changed on-the-go), it may be desired that the transitions between two planting depth settings and corresponding trench contours be uniform. That is, to be uniform, the trench contour when moving from a shallow planting depth to a deeper planting depth should be the same as the trench contour when moving from a deeper planting depth to a shallower planting depth.

This can be very difficult to achieve because the forces required by the actuator assembly 154 to go from a deep planting depth to a shallow planting depth are often much larger than to go in the opposite direction (from a shallow planting depth to a deeper planting depth). This is because the downforce on the row unit 106 is acting against the transition from a deep planting depth to a shallow planting depth. Therefore, in order to reduce the planting depth, the entire row unit 106 must be lifted against its weight and against any downforce provided by an active (pneumatic or hydraulic) or passive (mechanical spring) downforce system 126. Even if the downforce actuator 126 is dynamic (in that it can be controlled from the operator compartment or by a control system on-the-go), and even though the extra downforce added by the downforce actuator 126 can be relieved, there normally still remains significant force acting against the transition from deep to shallow planting depths due to the weight of the row unit 106, itself. When the downforce actuator 126 is not dynamic, then the difference in forces acting against the transition from deep to shallow versus the forces acting against the transition from shallow to deep are even significantly larger.

Because the forces acting against the change in planting depth are much different, depending upon the adjustment direction (e.g., deep to shallow or shallow to deep), it can be very difficult to achieve a uniform trench contour when moving from shallow to deep and deep to shallow. For instance, it can take more time to overcome the force on the row unit 106 when moving it in one direction than to overcome the force when moving it in the other direction. This can make the trench contour (the change from the current planting depth to the target planting depth much steeper in one direction than in the other. Further, attempting to actuate a depth setting mechanism (such assembly 154) without previously obtaining an estimation of the required actuation force can lead to unwanted behavior which is known as backlash. In a backlash scenario, where the actuation force is not known before attempting to make the depth setting adjustment, the planting depth may actually move in the wrong direction before it begins moving in the right direction. By way of example, when moving from a deep planting depth to a shallower planting depth, the entire force on the row unit (as described above) must be overcome. The depth setting actuator may not normally be active at all times. Therefore, if a locking mechanism, that is used to hold the row unit at a desired planting depth, is unlocked so that an adjustment can be made, then when starting to change the planting depth, the row unit 106 may begin moving to even a deeper planting depth before it begins moving to a shallower planting depth, which results in a very undesirable trench contour. However, the present system estimates the actuation force and actuation speed that are needed so that that force can be immediately applied when (or just prior to when) the depth setting mechanism is unlocked. This avoids the undesired trench contour where the planting depth may actually move in the wrong direction before it eventually moves to the target planting depth.

In accordance with one example, planting depth control system 278 illustratively controls the planting depth actuator assembly 154 such that it has the same adjustment characteristics independent of the direction of adjustment. It can also include information about the planting speed to allow the characteristics of the adjustment to be consistent in a georeferenced coordinate system so that the same trench contour can be achieved at different planting speeds.

Figure 10A:
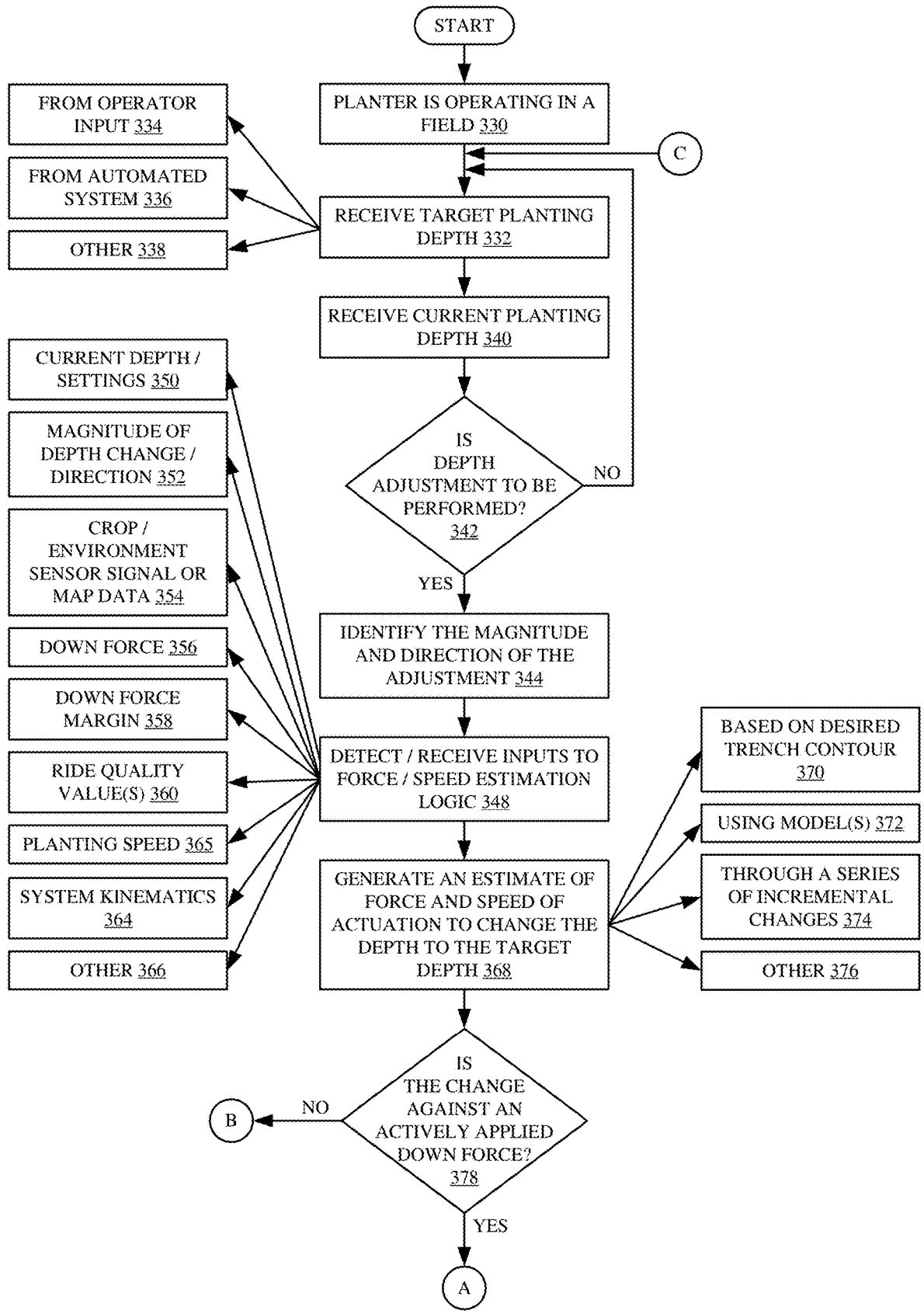
FIGS. 10A and 10B (collectively referred to herein as FIG. 10) show a flow chart illustrating one example of the operation of the planting depth control system shown in FIG. 9.
Figure 10B:
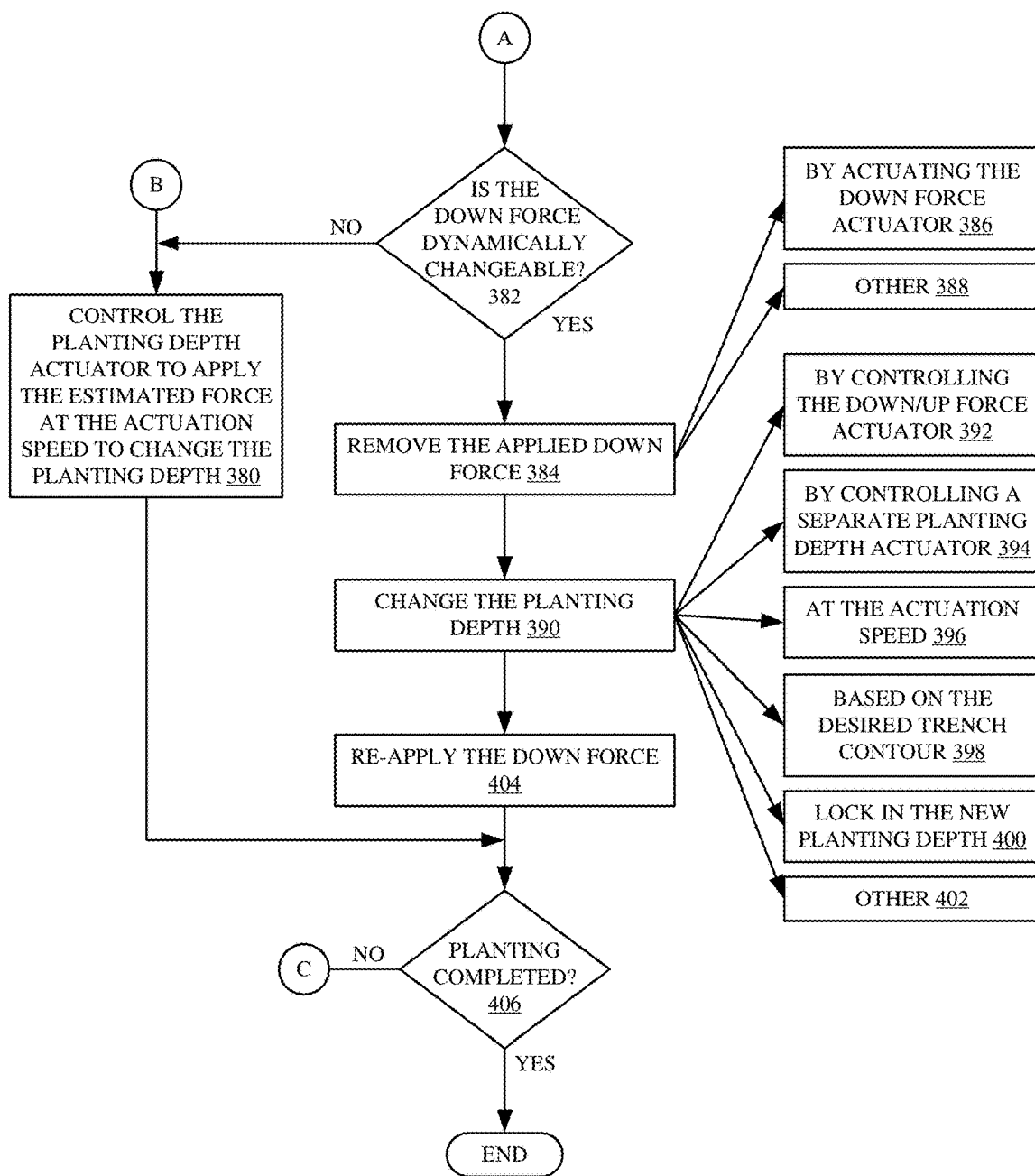

FIGS. 10A and 10B (collectively referred to herein as FIG. 10) illustrate a flow diagram showing one example of the operation of planting depth control system 278 and a row unit 106 of planting machine 100, in changing planting depth, in more detail. It is first assumed that planter 100 is operating in a field. This is indicated by block 330 in the flow diagram of FIG. 10. Force/speed estimation logic 292 then receives a target planting depth. This is indicated by block 332. Again, as discussed above, this can be based on an operator input 318. This is indicated by block 334. It can also be from an automated system, such as target depth identifying logic 290. This is indicated by block 336. It can be received in a wide variety of other ways as well, and this is indicated by block 338.

Adjustment identifying logic 303 then illustratively receives the target depth, and a current planting depth. This is indicated by block 340 in the flow diagram of FIG. 10. The current planting depth can be an estimated planting depth that is estimated based on sensor signals that sense the position of gauge wheels 116 and openers 114. It can also be a directly sensed planting depth that uses a planting depth sensor to sense the depth of the seed trench or furrow.

Adjustment identifying logic 303 then identifies whether an adjustment is to be performed based on the received target planting depth and the current planting depth. If so, it illustratively identifies a magnitude of the adjustment and a direction for the adjustment (such as how big the adjustment is and whether it is to be made to move the planting depth from shallower to deeper or deeper to shallower). It provides these items to force estimation model 304 and actuation speed estimation model 306. Determining whether an adjustment is to be performed, and the magnitude and direction of the adjustment, is indicated by blocks 342 and 344 in FIG. 10.

It will be noted that models 304 and 306 can be integrated into a single model that receives the inputs and generates outputs indicative of the estimated force and speed of actuation. They can be two separate models that process the inputs in parallel or sequential models where the output of one model feeds into the input of another model. All of these and other architectures are contemplated herein.

It will also be noted that force/speed estimation logic 292 (and models 304-306) can detect or receive a wide variety of inputs that can be used to generate the outputs. This is indicated by block 348. For instance, the inputs can include an input indicative of the current planting depth and the current actual planting depth setting. This is indicated by block 350. They can include the magnitude of the planting depth adjustment and direction of the planting depth adjustment as indicated by block 352. They can include a wide variety of crop or environmental sensor signal data or map data 354. This can include such things as crop characteristics sensed by crop characteristic sensors, environmental characteristics sensed by environmental characteristic sensors, topology information input by a topology map. Among a wide variety of other things. The inputs can also include the downforce 356 acting on the row unit 106 as well as the downforce margin 308. Examples of these are described above.

Logic 292 can receive a ride quality value 360 indicative of a ride quality of the row unit 106. This value can be generated by accelerometers that generate a signal indicative of accelerations measured on the row unit 106, or in other ways. It can receive a planting speed input 362 indicative of the ground speed of the planting machine 100. It can include an input identifying system kinematics (such as the measurements, angles, and other values that define the kinematics of the mechanisms used in adjusting planting depth). The system kinematics are indicated by block 364 in the flow diagram of FIG. 10. And it can include a wide variety of other inputs, such as gauge wheel position, or other items 366.

Force estimator model 304 and actuation speed estimation model 306 then generate an estimate of the force and speed of actuation to change the planting depth to the target depth. This is indicated by block 368. This can be based on a desired trench contour 370. The desired trench contour 370 may define how quickly the depth is to be changed or the magnitude of the change per lineal foot of trench, or other things. Thus, given the planting speed and the adjustment magnitude, the force and speed estimate may be output to change the planting depth based on the desired trench contour.

Again, the estimations can be generated using one or more models. This is indicated by block 372.

The depth adjustment can also be made through a series of incremental changes. This is indicated by block 374. By way of example, it may be desirable to make a planting depth adjustment in incremental steps. Therefore, the output of force/speed estimation logic 292 may be an output indicating how to control the planting depth actuator assembly 154 to move from the current planting depth to the target planting depth in a series of incremental steps. This may be done instead of controlling the actuator assembly 154 to move continuously from the current depth to the target depth. The estimate of force and speed of actuation to change the current planting depth to the target planting depth can be done in a wide variety of other ways as well, and this is indicated by block 376.

As discussed above, in one example, the force and speed estimates may be made in a system that does not have any additional applied downforce or that does not have a dynamically changeable downforce (such as in a system that does not have a hydraulic or pneumatic downforce actuator but is instead in a system that has a relatively static downforce system, such as one that imparts downforce through a set of mechanical springs or in other ways).

If, as indicated by block 378, the planting depth adjustment is not to be made against an actively applied downforce, then planting depth actuator control signal generator 312 illustratively controls the planting depth actuator assembly 154 to apply the estimated force (received from model 304) at the actuation speed (received from model 306) to change the planting depth. This is indicated by block 380. Again, this can be provided as a continuous signal to continuously actuate the actuator assembly 154 (e.g., to turn the lead screw 180 or other actuator) to move the gauge wheel arms 148 to change the planting depth in one continuous control step. It can also be done by making incremental changes that incrementally move the gauge wheel arms 148 to change the planting depth incrementally, from the current planting depth to the target planting depth. It can be made in other ways as well.

If, at block 378, it is determined that the planting depth change is to be made against an actively applied downforce, then, at block 382, downforce control signal generator 310 determines whether the downforce is applied by a dynamically changeable system, or whether it is a relatively static (e.g., mechanical spring-based) system. If there is an active downforce applied to the row unit, but it is not dynamically changeable, then, processing again continues at block 380 where planting depth actuator control signal generator 312 generates control signals to control the planting depth actuator assembly 154 to change the planting depth as discussed above.

However, if, at block 382, it is determined that the actively applied downforce is dynamic in nature, and that it can be controlled on-the-fly, then downforce control signal generator 310 generates control signals to control downforce actuator 126 to remove the actively applied downforce. This is indicated by block 384. In the example described herein, this is done by controlling the downforce actuator 126 to become passive or to control the actuator to actively remove the downforce in other ways as well. This is indicated by blocks 386 and 388. Also, in one example, the row unit can be temporarily lifted out of the ground so that the actively applied downforce is no longer working against the depth setting change (e.g., change can be made during a headland turn or during a brief pause while the row unit 106 is lifted out of the ground). These are examples only.

Planting depth actuator control signal generator 312 then generates control signals 316 to control the planting depth actuator assembly 154 to change the planting depth. This is indicated by block 390 in the flow diagram of FIG. 10. It will be noted that, as described above, the planting depth actuator assembly 154 may be incorporated into the downforce actuator 126, so that the downforce actuator 126 also includes an upforce actuator that can exert upforce on the row unit, instead of just downforce. In that case, the upforce actuator can be controlled in making the planting depth change as well. This is indicated by block 392. The planting depth can be changed by controlling a separate planting depth actuator assembly 154, as discussed above. This is indicated by block 394. The actuator (e.g., the motor) in the planting depth actuator assembly 154 can be controlled at the estimated actuation speed so that the planting depth adjustment is made over a certain period of time. This is indicated by block 396. The planting depth actuator assembly 154 can be controlled based on a desired trench contour. For instance, it can be controlled to make the adjustment, while considering the speed of the planting machine 100, so that the change from the current depth to the target depth is made according to a desired trench contour (so that the trench does not change depth too rapidly over a given lineal distance) or otherwise. Controlling the planting depth actuator assembly based on a desired trench contour is indicated by block 398.

Once the new planting depth is achieved, then planting depth actuator control signal generator 312 generates control signals to control the planting depth actuator assembly 154 to lock the new planting depth in place. This is indicated by block 400. By way of example, it may be that the planting depth actuator assembly 154 includes a worm drive. In that case, once the target planting depth is achieved, the worm drive is self-locking. In another example, the new planting depth can be locked in other ways so that forces or accelerations applied to the row unit 106 through the gauge wheels 116 do not transmit back to the actuator (e.g., the electric motor or other motor) in the planting depth actuator assembly 154. Instead, those forces or accelerations are illustratively transmitted to the frame of the planting machine, such as the shank 152, or other structural mechanisms.

The planting depth adjustment can be made in a wide variety of other ways as well. This is indicated by block 402 in the flow diagram of FIG. 10.

Once the planting depth adjustment has been made and locked in, then downforce control signal generator 310 illustratively controls downforce actuator 126 to reapply the active downforce that was removed at block 384. Reapplying the downforce after the planting depth adjustment is made is indicated by block 404 in the flow diagram of FIG. 10.

It will be appreciated that, in one example, planting depth control system 278 can continue to monitor various sensor signals and other inputs and make planting depth changes, on-the-go, until the planting operation is completed. This is indicated by block 406 in the flow diagram of FIG. 10.

Figure 11:
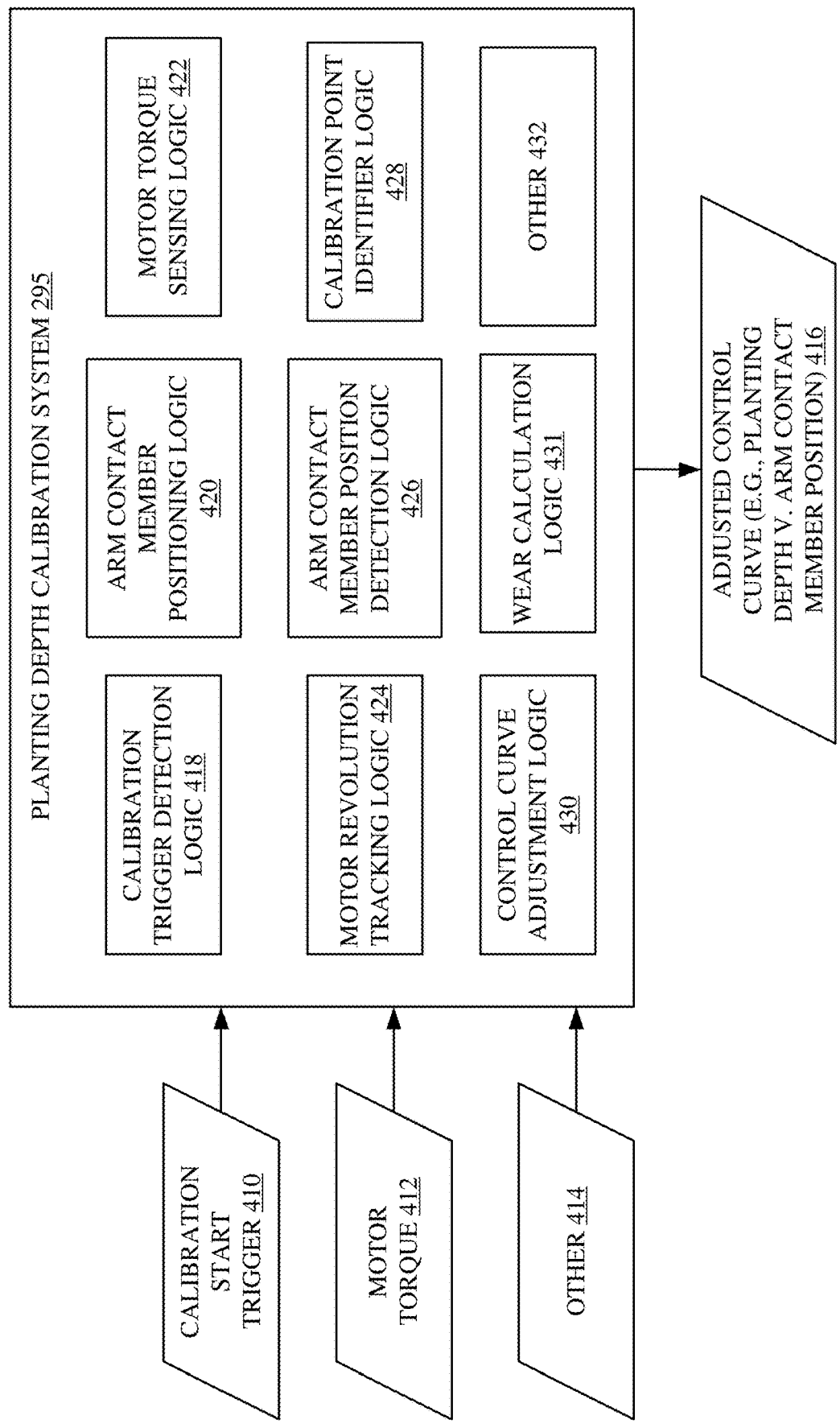
FIG. 11 is a block diagram of one example of a planting depth calibration system in more detail.

FIG. 11 is a block diagram of one example of planting depth calibration system 295. In the example shown in FIG. 11, system 295 is seen receiving a calibration start trigger 410, motor torque signal 412, and it can receive a wide variety of other items 414. Based on the received items, it outputs an adjusted control curve 416 that planting depth control system 278 can use to control planting depth. As discussed above, control signal generator logic 294 can access a control curve that plots desired planting depth versus an indication of position of the mechanical stop 150. However, the position of mechanical stop 150 is determined based upon the kinematics of the physical system (such as the measurements, angles, physical relationships, etc., in portions of the row unit and planting depth actuator assembly 154 that are used to set planting depth). The various kinematic values can be obtained at the time of manufacture, or they can be input later. Some of those values can also be sensed.

There are some conditions under which the kinematic values may change. For instance, as a row unit 106 is used, the openers 114 and gauge wheels 116 may exhibit wear. This can cause their diameters to change, and they may not change uniformly with respect to one another. Therefore, the position of mechanical stop 150, as it bears against gauge wheel arms 148, may result in a different planting depth than before the gauge wheels 116 and openers 114 had worn. Also, the kinematic values used to generate the control curve may change based on manufacturing and assembly tolerances. Therefore, from one row unit to the next, the kinematic values may be slightly different, even when the parts are new. These and other factors can affect the kinematic values and can thus affect the relationship between the position of mechanical stop 150 along lead screw 180, and the resulting planting depth. Thus, planting depth calibration system 295 can intermittently run a calibration process that adjusts the control curve based upon the new kinematic values identified during the calibration process. The adjusted control curve 416 can then be used by planting depth control system 278 to control planting depth.

In the example shown in FIG. 11, planting depth calibration system 295 illustratively includes calibration trigger detection logic 418, arm contact member position logic 420, motor torque sensing logic 422, motor revolution tracking logic 424, arm contact member position detection logic 426, calibration curve zero point identifier logic 428, control curve adjustment logic 430, wear calculation logic 431, and it can include a wide variety of other items 432. Before describing the operation of system 295 in more detail, a brief description of some of the items in system 295, and their operation, will first be provided.

Calibration trigger detection logic 418 detects a calibration start trigger 410 that indicates that a calibration operation is to be performed. This can include an operator input, or it can include an automated trigger, such as where the system monitors a number of acres that have been planted since the last calibration process was performed. These and other triggers are discussed below.

Arm contact member positioning logic 420 illustratively generates an output to control signal generator logic 294 (shown in FIG. 9) to generate control signals to move mechanical stop (or arm contact member) 150 to a desired position along lead screw 180. Motor torque sensing logic 422 illustratively receives a motor torque signal 412 indicative of the torque of the motor driving lead screw 180, in planting depth actuator assembly 154. Motor revolution tracking logic 424 can include a revolution sensor, or another sensor that senses a number of revolutions performed by the output of the motor driving lead screw 180. Arm contact member position detection logic 426 illustratively detects the position of the mechanical stop (or arm contact member) 150. This is described in greater detail below. Calibration curve zero point identifier logic 428 illustratively identifies a new calibration point, and control curve adjustment logic 430 recalibrates (or adjusts) the control curve, based upon calibration points that are identified during the calibration operation. Wear calculation logic 431 can calculate wear on opener 114 and/or gauge wheels 116. This is also discussed in greater detail below.

As mentioned, control curve adjustment logic 430 adjusts the control curve based upon the calibration points identified by calibration point identifier logic 428. In one example, the calibration process can be performed for a plurality of different calibration points, and the control curve can be adjusted based upon all of those points. In another example, the calibration process can be run to identify a single calibration point, and the control curve can be adjusted based upon that calibration point.

Figure 12A:
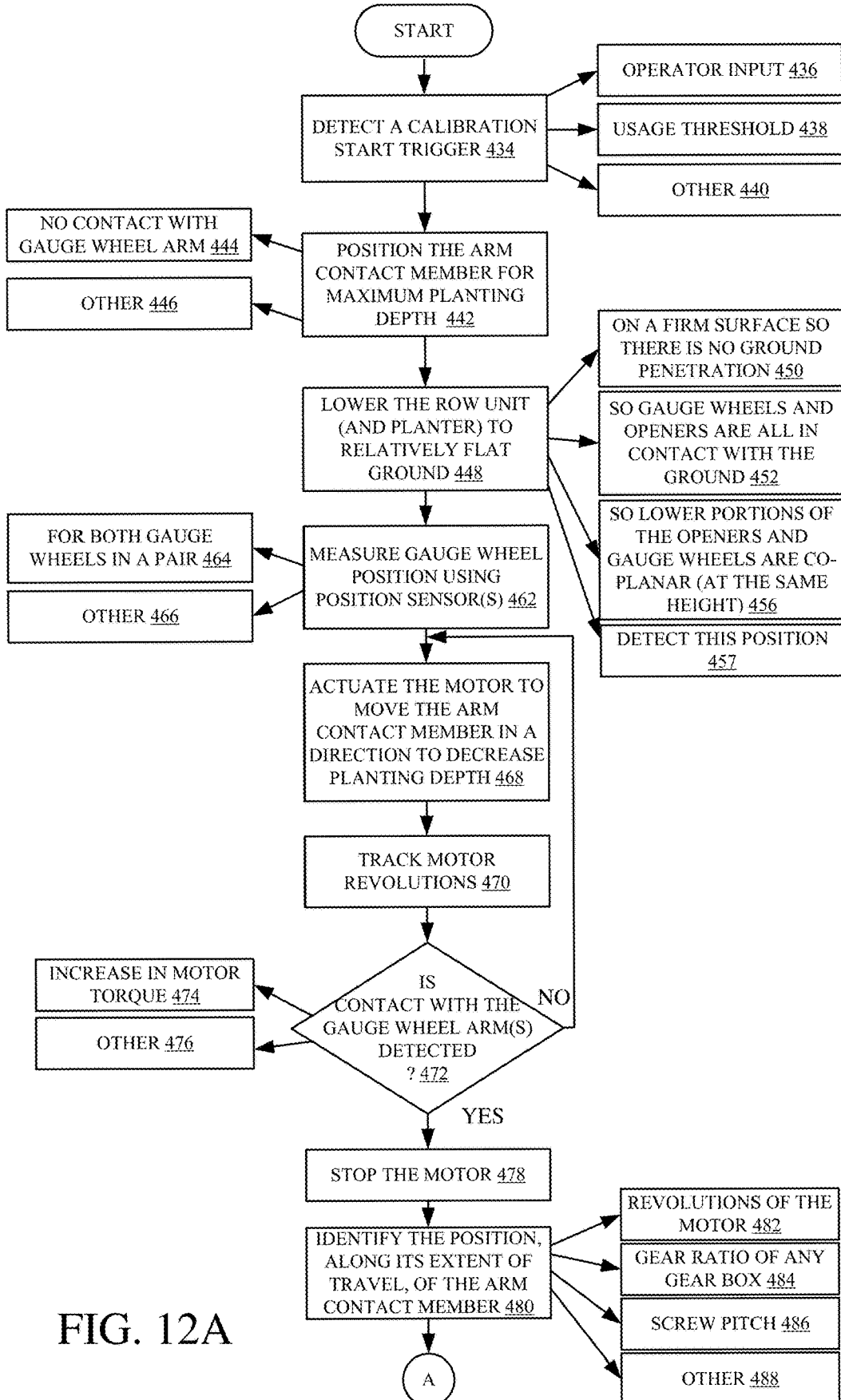
FIG. 12A-12C (hereinafter referred to as FIG. 12) are flow diagrams illustrating one example of the operation of the planting depth calibration system in more detail.
Figure 12B:
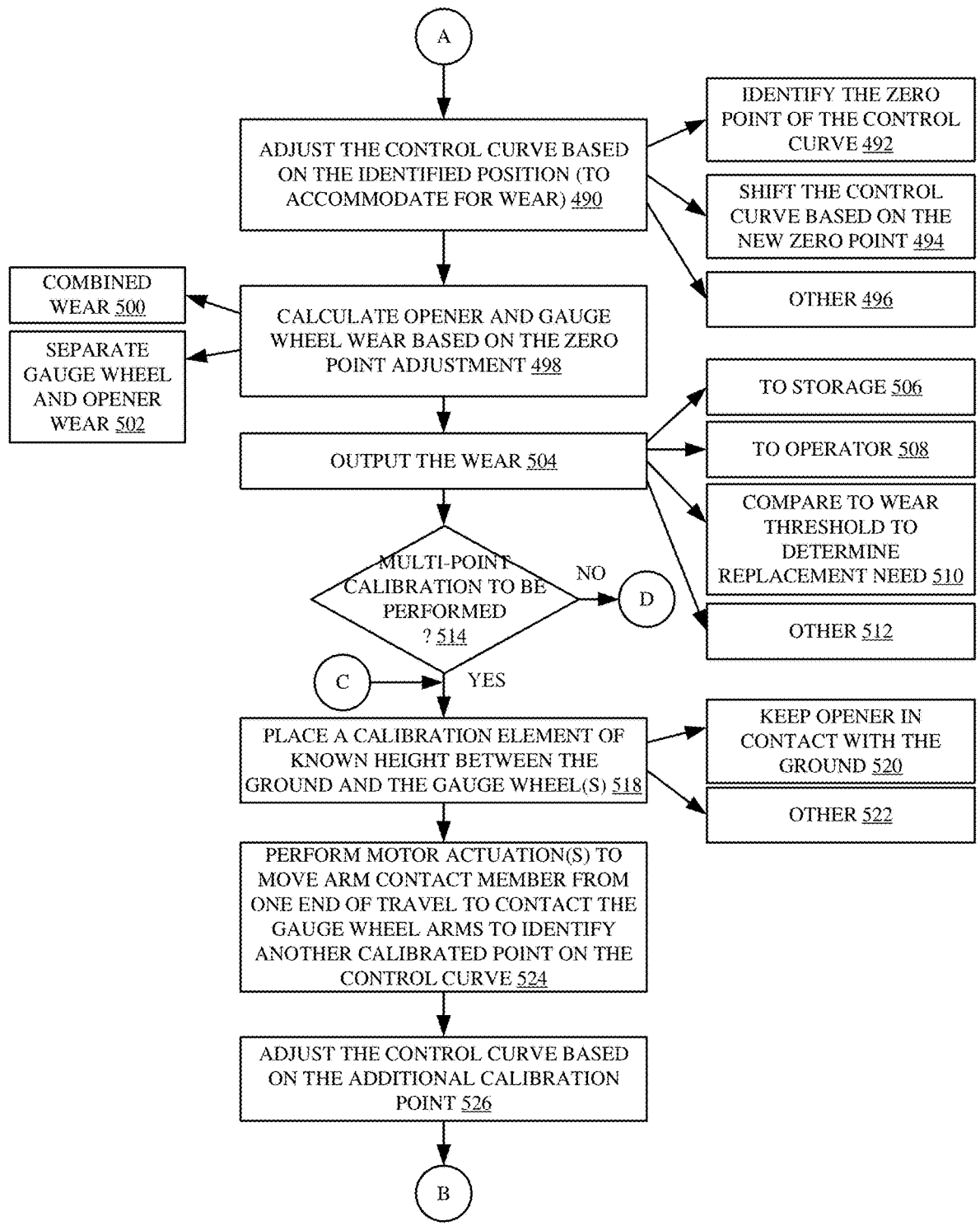
Figure 12C:
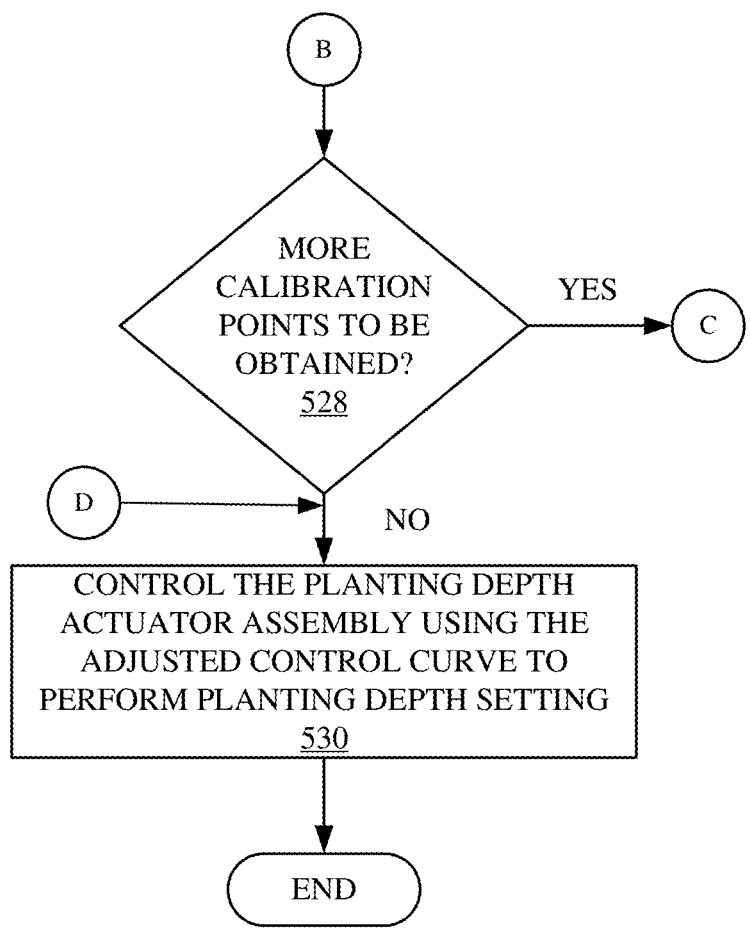

FIGS. 12A-12C (hereinafter referred to as FIG. 12) show a flow diagram illustrating one example of the operation of planting depth calibration system 295 in performing a calibration process. FIGS. 13A-13D are pictorial/schematic illustrations of a portion of row unit 106, to illustrate different parts of the calibration process. Some items in FIGS. 13A-13D are similar to those shown in FIG. 4, and they are similarly numbered. FIGS. 12A-13D will now be described in conjunction with one another.

In one example, calibration trigger detection logic 418 first detects a calibration start trigger. This is indicated by block 434 in the flow diagram of FIG. 12. The calibration start trigger 410 can take a variety of different forms. For instance, it can be an operator input 436, or it can be an indication that a usage threshold has been reached, as indicated by block 438. For example, the calibration start trigger 410 can be generated when control system 260 determines that a row unit has been used to plant a threshold number of acres, or that it has been used for a threshold amount of time. In another example, usage threshold 438 can be determined based on the soil type, so that if the soil is more likely to promote wear, then the trigger is generated earlier than if the soil is less likely to promote wear. The calibration start trigger can be generated based on a wide variety of other criteria that may indicate wear as well, and this is indicated by block 440.

Once the calibration start trigger has been detected, then arm contact member positioning logic 420 positions the arm contact member (or mechanical stop) 150 for maximum planting depth. This is indicated by block 442. One example of this is illustrated in the pictorial illustration shown in FIG. 13A. It can be seen that arm contact member 150 has been moved to its position closest to bearing 182 (or to another known position along its extent of travel). It is also out of contact with gauge wheel arm 138. This is indicated by block 444 in the flow diagram of FIG. 12. The arm contact member 150 can be positioned for maximum planting depth in other ways as well, and this is indicated by block 446.

Next, the row unit 106 is lowered (and the entire planter can be lowered) to relatively flat ground. This is indicated by block 448. In one example, the ground may be a firm surface, such as concrete, so that neither gauge wheel 116 nor opener 114 penetrate the ground. This is indicated by block 450. It is also controlled so that both gauge wheels 116 and opener 114 are in contact with the ground as indicated by block 452. This ensures that the lower portions of openers 114 and gauge wheels 116 are generally coplanar, in a horizontal plane, generally defined by the ground surface 454. This is also indicated by block 456 and can be detected automatically or through observation as indicated by block 457 in the flow diagram of FIG. 12.

Figure 13A:
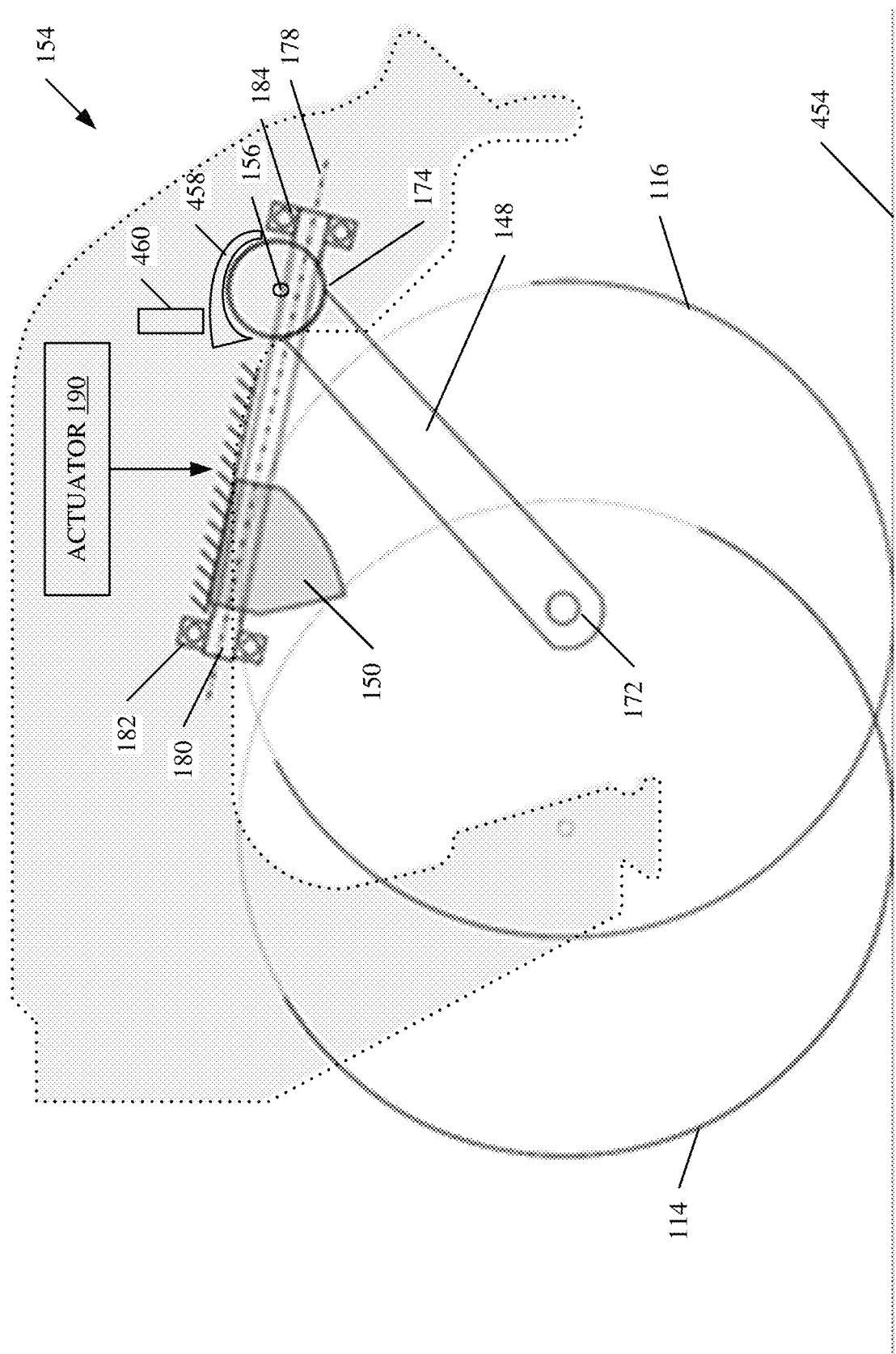
FIGS. 13A-13D are pictorial/schematic illustrations showing calibration steps.

FIG. 13A also shows that, in one example, gauge wheel arms 148 include a sensor target 458, along with a distance sensor 460 (which may be an inductive sensor, or another sensor) that measures the distance to target 458. Target 458 is tapered so that, as gauge wheel arm 148 pivots about pivot point 156, the distance between sensor 460 and target 458 changes approximately linearly (or in another known relationship) with the change of the gauge wheel angle.

Returning again to the flow diagram of FIG. 12, once the row unit 106 is lowered onto the relatively flat ground, then the arm contact member position detection logic 426 measures the gauge wheel position using position sensor 460 and target 458, or another sensor. This is indicated by block 462 in the flow diagram of FIG. 12. In one example, the measurement is taken for both gauge wheels in a pair of gauge wheels, as indicated by block 464. The measurement can be made in other ways as well, and this is indicated by block 466.

Arm contact member positioning logic 420 then generates a control signal and provides it to control signal generator logic 294 to actuate the motor to move the mechanical stop (or arm contact member) 150 in a direction to decrease planting depth. Referring again to FIG. 13A, this will cause mechanical stop 150 to move more towards bearing 184. Actuating the motor to move mechanical stop 150 in this direction is indicated by block 468 in the flow diagram of FIG. 12. While this is happening, motor revolution tracking logic 424 tracks the number of revolutions of the motor, as it is moving mechanical stop 150. Tracking the motor revolutions is indicated by block 470.

Figure 13B:
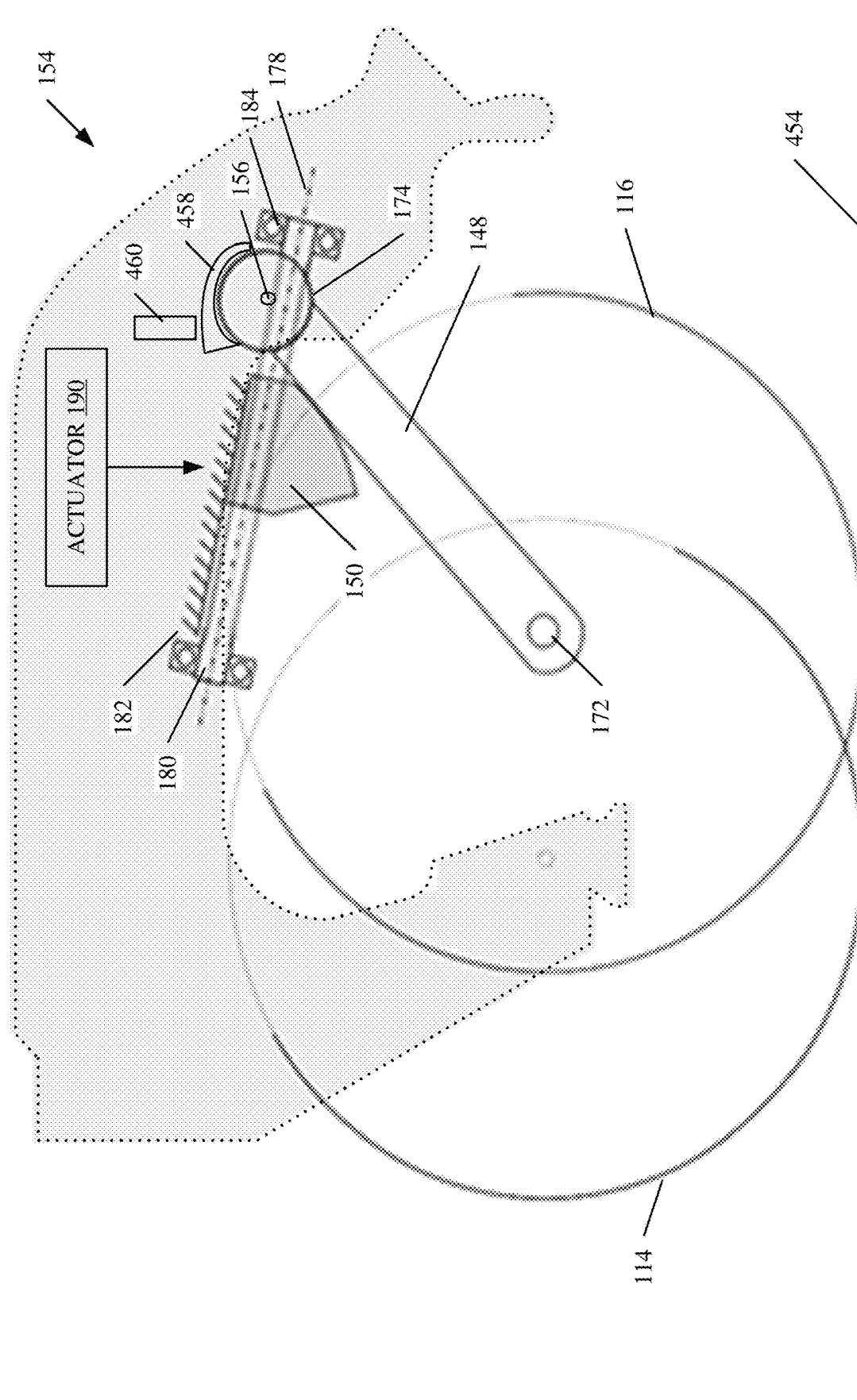

This continues until motor torque sensing logic 422 senses that mechanical stop 150 has come into contact with gauge wheel arm 148, as is illustrated in the pictorial diagram shown in FIG. 13B. In one example, when this occurs, the torque output by the motor turning lead screw 180 will increase, and this will be indicated by motor torque signal 412. When this occurs, arm contact member positioning logic 420 outputs a signal to control signal generator logic 294 so that it stops rotation of the motor. Determining that mechanical stop 150 is in contact with the gauge wheel arm 148, such as through an increase in motor torque or otherwise, is indicated by blocks 472, 474 and 476 in FIG. 12. Stopping the motor once mechanical stop 150 comes into contact with gauge wheel arm 148 is indicated by block 478.

Arm contact member position detection logic 426 then determines the position, along its extent of travel, of the arm contact member (or mechanical stop) 150. This is indicated by block 480 in the flow diagram of FIG. 12. This can be done in a variety of different ways. For instance, using the number of revolutions of the motor, as indicated by block 482 that were required to move mechanical stop 150 from the position shown in FIG. 13A to the position shown in FIG. 13B, along with the gear ratio of any gear box that is deployed between the motor drive shaft and lead screw 180 (as indicated by block 484), along with the pitch of the screw on lead screw 180 (as indicated by block 486), logic 426 can identify how far mechanical stop 150 has moved through its extent of motion along lead screw 180. The position along its extent of travel can be identified in other ways as well, and this is indicated by block 488.

Once this position is known, calibration point identifier logic 428 illustratively identifies this as a zero point on the calibration curve, where gauge wheel 116 and opener 114 are at the exact same height so the corresponding planting depth would be zero. Control curve adjustment logic 430 then adjusts the control curve based upon the identified calibration zero point. This is indicated by block 490 in the flow diagram of FIG. 12. Identifying this calibration point as a zero point on the control curve is indicated by block 492. It illustratively shifts the control curve based on the new zero point, and this is indicated by block 494. It can adjust the control curve to accommodate for wear or other changes in the kinematics of the system in other ways as well, and this is indicated by block 496.

Wear calculation logic 431 then illustratively calculates the wear on the opener and gauge wheels. This is indicated by block 498. In one example, where a gauge wheel position sensor 460 is used, and where arm contact member position detection logic 426 is also used (which calculates the position of mechanical stop 150 based upon the revolutions of the motor and the gear ratio and screw pitch), then wear calculation logic 431 can calculate the wear on both the gauge wheel 116 and on the opener 114. However, where only one of those position sensors is used, then the combined wear of both the opener 114 and gauge wheel 116 can be calculated. Calculating combined wear is indicated by block 500 and calculating separate gauge wheel and opener wear is indicated by block 502.

Wear calculation logic 431 then outputs and indication of the wear on the gauge wheels 116, and the opener 114, and this is indicated by block 504. It can be output to a storage component as indicated by block 506, where it can be accessed at any time. It can also be displayed to the operator as indicated by block 508. In one example, wear calculation logic 431 compares the calculated wear to a wear threshold to determine whether replacement of gauge wheels 116 or opener 114 is needed. This is indicated by block 510. If so, that can be brought to the operator's attention (or another's attention) through an alert message, or another type of output mechanism. Outputting the wear can be done in other ways as well, and this is indicated by block 512.

As discussed above, planting depth calibration system 295 can perform either single point calibration (where a single calibration point is identified, as discussed above with respect to FIG. 12) or it can perform a multi-point calibration where multiple calibration points can be identified and used to adjust the calibration curve. If multi-point calibration is to be performed, as indicated by block 514, then, in one example, a calibration element (illustrated by element 516 in FIGS. 13C and 13D), is placed between the ground and the gauge wheels 114, while allowing opener 114 to remain in contact with the ground. In one example, the calibration element 516 has a known height. This is indicated by block 518 in the flow diagram of FIG. 12. Keeping the opener 114 in contact with the ground is indicated by block 520. The calibration element 516 can be placed under the gauge wheels on a single row unit 106, or under all gauge wheels, of all row units 106 on a planter. The calibration element can be placed between the ground and the gauge wheels in other ways as well, and this is indicated by block 522.

Figure 13C:
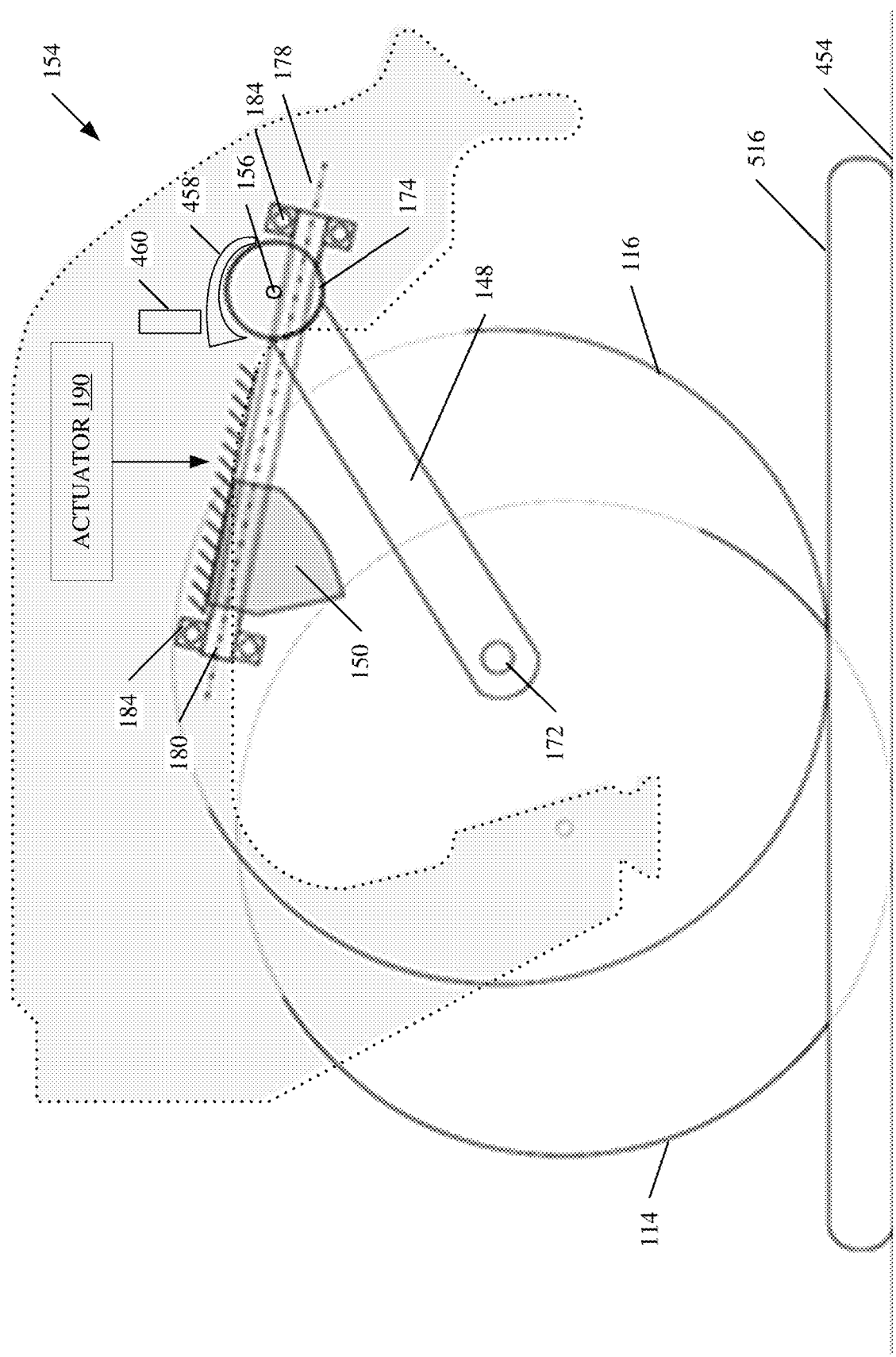
Figure 13D:
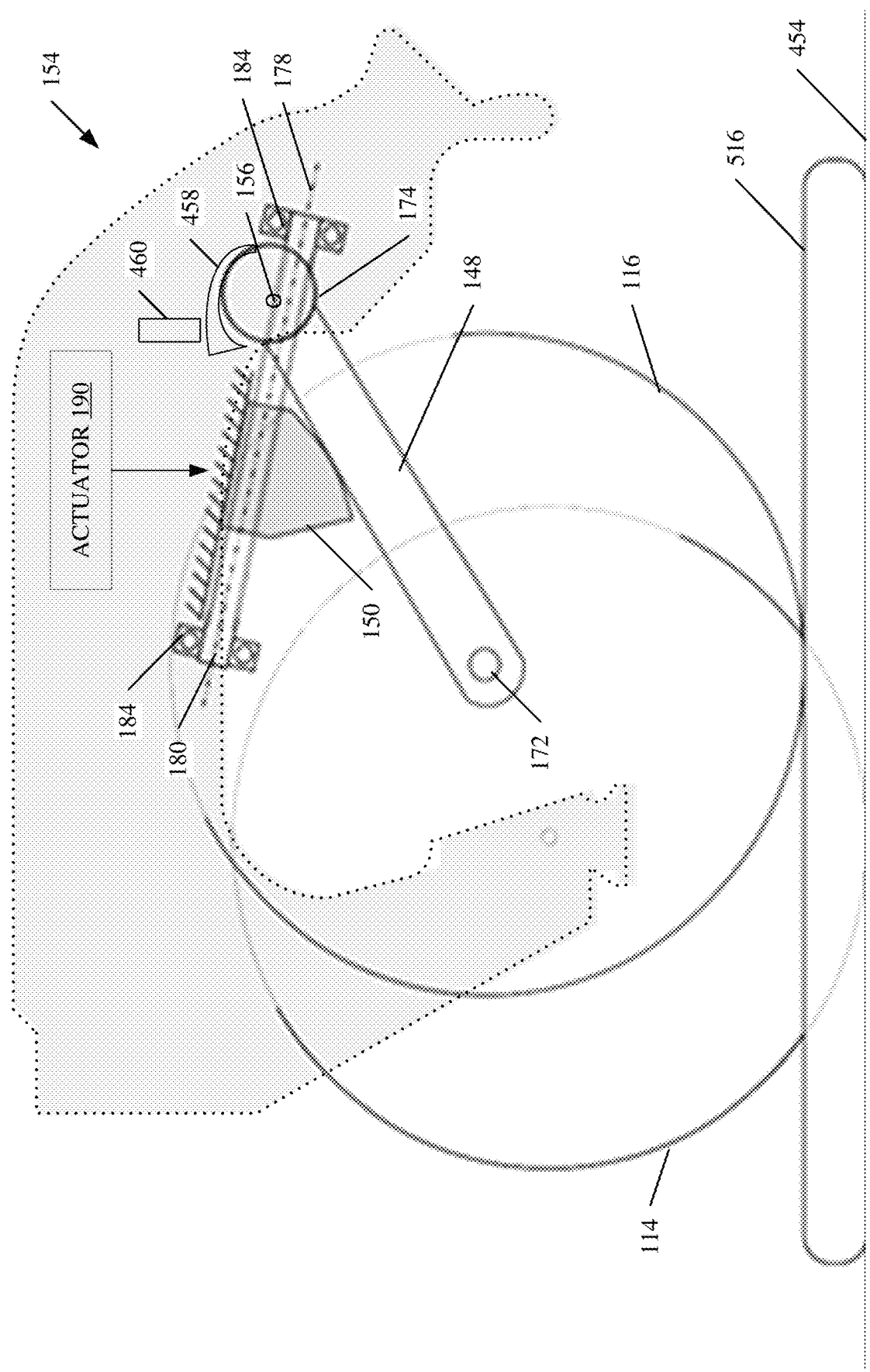

Planting depth calibration system 295 then performs the motor actuations to the move the arm contact member 150 from one end of travel to contact the gauge wheel arms 148 in order to identify another calibration point on the control curve. This is indicated by block 524 in the flow diagram of FIG. 12, and it is described in greater detail above with respect to FIGS. 13A and 13B. It is also shown in more detail in FIG. 13C and FIG. 13D. For instance, FIG. 13C shows that arm contact member 150 is in its furthest extent of travel toward bearing 182. FIG. 13D shows that arm contact member 150 has now been moved until it comes into engagement with gauge wheel arm 148. Again, this can be sensed based on an increase in torque at the output of the motor driving lead screw 180, or in other ways.

Once the distance traveled by member 150 has been identified (based on the rotations of the motor, any gear ratio, the pitch of lead screw 180, etc.), then this, in combination with the known offset between opener 114 and gauge wheels 116 (based on the known height of calibration element 516), can be used to identify another calibration point. Calibration point identifier logic 428 identifies that calibration point, and control curve adjustment logic 430 adjusts the control curve again, based upon the newly identified calibration point. Adjusting the control curve based on the additional calibration point is indicated by block 526 in the flow diagram of FIG. 12.

If additional calibration elements 516, that have different, known heights are provided, then the same process can be repeated to identify still more calibration points that can be used to adjust the calibration curve. If more calibration points are to be identified, as indicated by block 528 in the flow diagram of FIG. 12, the processing reverts to block 518.

If not, however, then the planting depth control system 578 illustratively controls the planting depth actuator assembly 154 using the adjusted control curve 416. This is indicated by block 530 in the flow diagram of FIG. 12.

The present discussion has mentioned processors and servers. In one embodiment, the processors and servers include computer processors with associated memory and timing circuitry, not separately shown. They are functional parts of the systems or devices to which they belong and are activated by, and facilitate the functionality of the other components or items in those systems.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

It will also be noted that the elements of FIGS. 8 and 9, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 14:
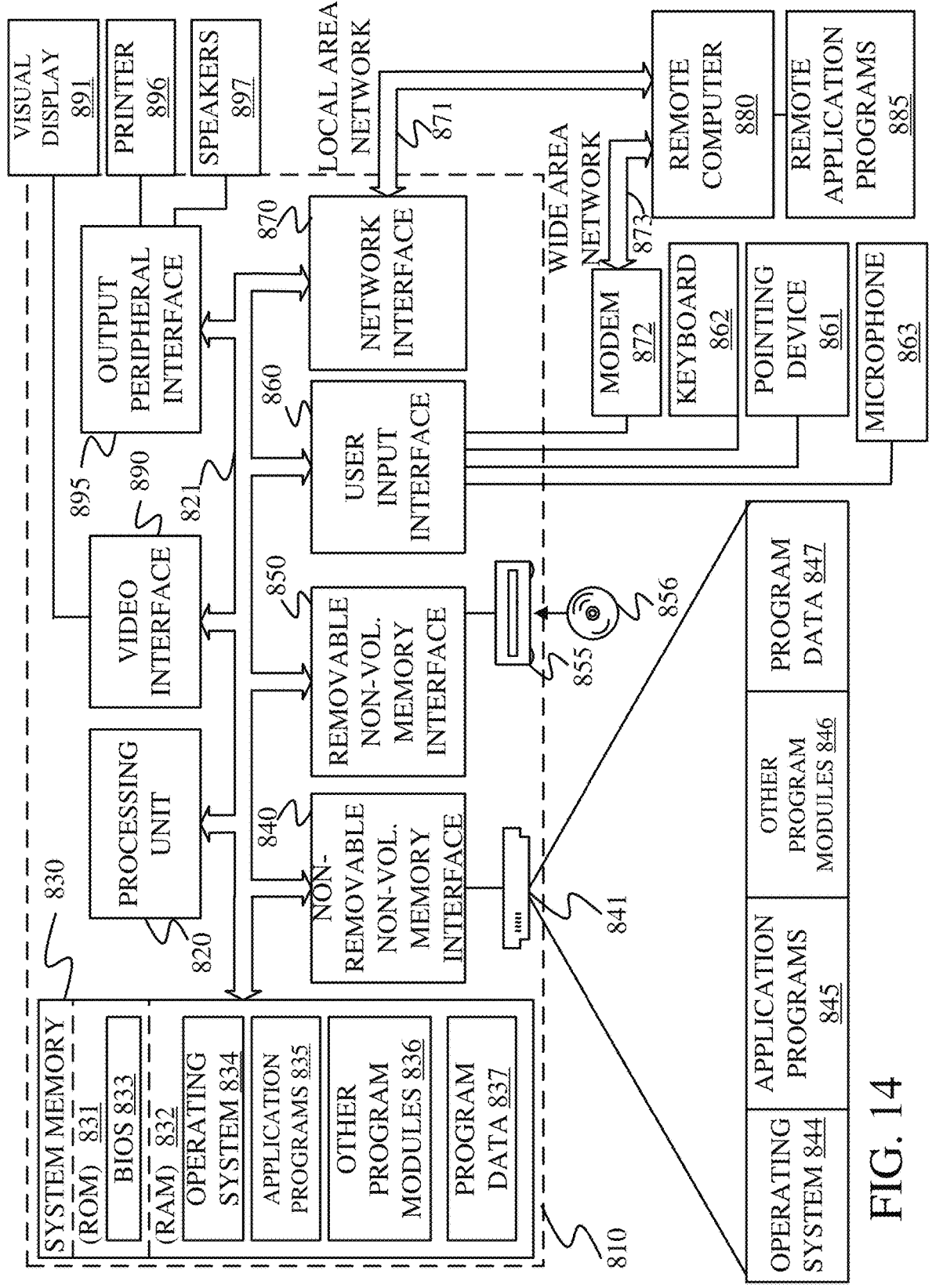
FIG. 14 is a block diagram of one example of a computing environment that can be used in the architectures shown in the previous figures.

FIG. 14 is one example of a computing environment in which elements of FIGS. 8-9, or parts of them, (for example) can be deployed. With reference to FIG. 14, an example system for implementing some embodiments includes a general-purpose computing device in the form of a computer 810. Components of computer 810 may include, but are not limited to, a processing unit 820 (which can comprise processors or servers shown in previous FIGS.), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIGS. 8-9 can be deployed in corresponding portions of FIG. 14.

Computer 810 typically includes a variety of computer readable media. Computer readable media can be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile discs (DVD) or other optical disc storage, magnetic cassettes, magnetic tape, magnetic disc storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 14 illustrates operating system 834, application programs 835, other program modules 836, and program data 837.

The computer 810 may also include other removable/non-removable volatile/nonvolatile computer storage media. By way of example only, FIG. 14 illustrates a hard disc drive 841 that reads from or writes to non-removable, nonvolatile magnetic media, an optical disc drive 855, and nonvolatile optical disc 856. The hard disc drive 841 is typically connected to the system bus 821 through a non-removable memory interface such as interface 840, and optical disc drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 14, provide storage of computer readable instructions, data structures, program modules and other data for the computer 810. In FIG. 14, for example, hard disc drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a local area network—LAN, or wide area network WAN, a controller area network CAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 14 illustrates, for example, that remote application programs 885 can reside on remote computer 880.

It should also be noted that the different embodiments described herein can be combined in different ways. That is, parts of one or more embodiments can be combined with parts of one or more other embodiments. All of this is contemplated herein.

Example 1 is a method of controlling a planting depth actuator, comprising:
controlling the planting depth actuator to position an arm contact member, that moves along an axis of movement through an extent of travel and that contacts a gauge wheel arm to change a relative position of a gauge wheel relative to an opener on a planter row unit, at a first known position along the extent of travel and out of contact with the gauge wheel arm;
detecting that the row unit is positioned so the gauge wheel and the opener are in a known position relative to one another;
controlling the planting depth actuator to move the arm contact member from the first known position to a second position in which the arm contact member is in contact with the gauge wheel arm;
identifying how far the arm contact member moved along the extent of travel from the first, known position to the second position, to identify the second position as a first calibration point; and
adjusting a control curve, used to position the arm contact member to control planting depth of the row unit, based on the first calibration point.

Example 2 is the method of any or all previous examples wherein controlling the planting depth actuator to position the arm contact member at the first, known position, comprises:
controlling the planting depth actuator to move the arm contact member to a first end of the extent of travel.

Example 3 is the method of any or all previous examples and further comprising:
detecting when the arm contact member is in contact with the gauge wheel arm.

Example 4 is the method of any or all previous examples wherein detecting when the arm contact member is in contact with the gauge wheel arm comprises:
detecting an increase in torque output by the planting depth actuator.

Example 5 is the method of any or all previous examples wherein the planting depth actuator comprises a motor with a rotatable output shaft that drives rotation of a lead screw that rotates to drive the arm contact member along the axis of movement and wherein controlling the planting depth actuator to move the arm contact member from the first known position to the second position, comprises:
controlling the motor to rotate the rotatable output shaft.

Example 6 is the method of any or all previous examples wherein identifying how far the arm contact member moved comprises:
counting a number of rotations of the rotatable output shaft and identifying how far the arm contact member moved based on the number of rotations and a pitch of the lead screw.

Example 7 is the method of any or all previous examples wherein the rotatable out shaft is coupled to the lead screw through a gear mechanism having a gear ratio and wherein identifying how far the arm contact member moved comprises:
counting the number of rotations of the rotatable output shaft and identifying how far the arm contact member moved based on the number of rotations and the pitch of the lead screw and the gear ratio.

Example 8 is the method of any or all previous examples and further comprising:
identifying wear of the opener and the gauge wheel based on the first calibration point.

Example 9 is the method of any or all previous examples and further comprising:
sensing a position of the gauge wheel and wherein identifying wear comprises identifying wear of the opener and the gauge wheel, separately, based on the position of the gauge wheel and the first calibration point.

Example 10 is a planting depth control system, comprising:
control signal generator logic that generates control signals to control an actuator to position an arm contact member along an axis of movement through an extent of travel and that contacts a gauge wheel arm to change a relative position of a gauge wheel relative to an opener on a planter row unit;
a position detector detecting that the row unit is positioned so the gauge wheel and the opener are in a known position relative to one another;
arm contact member positioning logic that generates a position output to the control signal generator logic to position the arm contact member at a first known position along the extent of travel and out of contact with the gauge wheel arm and to move the arm contact member from the first known position to a second position in which the arm contact member is in contact with the gauge wheel arm;
a planting depth calibration system that identifies how far the arm contact member moved along the extent of travel from the first, known position to the second position, to identify the second position as a first calibration point; and
control curve adjustment logic that adjusts a control curve, used to position the arm contact member to control planting depth of the row unit, based on the first calibration point.

Example 11 is the planting depth control system of any or all previous examples wherein the arm contact member position logic is configured to control the actuator to position the arm contact member at the first, known position, buy controlling the actuator to move the arm contact member to a first end of the extent of travel.

Example 12 is the planting depth control system of any or all previous examples and further comprising:
a first position detector configured to detect when the arm contact member is in contact with the gauge wheel arm.

Example 13 is the planting depth control system of any or all previous examples wherein the first position detector comprises:
motor torque sensing logic detecting an increase in torque output by the actuator.

Example 14 is the planting depth control system of any or all previous examples wherein the actuator comprises a motor with a rotatable output shaft that drives rotation of a lead screw that rotates to drive the arm contact member along the axis of movement and wherein the planting depth calibration system, comprises:
motor revolution tracking logic configured to track a number of revolutions of the rotatable output shaft; and
arm contact member position detection logic identifying how far the arm contact member moved based on the number of revolutions and a pitch of the lead screw.

Example 15 is the planting depth control system of any or all previous examples wherein the rotatable out shaft is coupled to the lead screw through a gear mechanism having a gear ratio and wherein the arm contact member positioning logic is configured to identify how far the arm contact member moved based on the number of revolutions and the pitch of the lead screw and the gear ratio.

Example 16 is the planting depth control system of any or all previous examples and further comprising:
  wear identifying logic configured to identify wear of the opener and the gauge wheel based on the first calibration point.

Example 17 is the planting depth control system of any or all previous examples and further comprising:
  a gauge wheel position sensor sensing a position of the gauge wheel and wherein the wear identifying logic identifies wear of the opener and the gauge wheel, separately, based on the position of the gauge wheel and the first calibration point.

Example 18 is a method of controlling a planting depth actuator, comprising:
  controlling the planting depth actuator to position an arm contact member, that moves along an axis of movement through an extent of travel and that contacts a gauge wheel arm to change a relative position of a gauge wheel relative to an opener on a planter row unit, at a first end position along the extent of travel and out of contact with the gauge wheel arm;
  detecting that the row unit is positioned so a lowest position of the gauge wheel and a lowest position of the opener are in a known position relative to one another;
  controlling the planting depth actuator to move the arm contact member from the first end position to a second position in which the arm contact member is in contact with the gauge wheel arm;
  identifying how far the arm contact member moved along the extent of travel from the first end position to the second position, to identify the second position as a first calibration point; and
  adjusting a control curve, used to position the arm contact member to control planting depth of the row unit, based on the first calibration point.

Example 19 is the method of any or all previous examples wherein the actuator comprises a motor with a rotatable output shaft that drives rotation of a lead screw that rotates to drive the arm contact member along the axis of movement and wherein controlling the actuator to move the arm contact member from the first known position to the second position comprises controlling the motor to rotate the rotatable output shaft and wherein identifying how far the arm contact member moved comprises:
  counting a number of rotations of the rotatable output shaft and identifying how far the arm contact member moved based on the number of rotations and a pitch of the lead screw.

Example 20 is the method of any or all previous examples and further comprising:
  sensing a position of the gauge wheel; and identifying wear of the opener and the gauge wheel, separately, based on the position of the gauge wheel and the first calibration point.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method of controlling a planting depth actuator, comprising:
  controlling the planting depth actuator to position an arm contact member, that moves along a path of movement through an extent of travel and that contacts a gauge wheel arm to change a relative position of a gauge wheel relative to an opener on a planter row unit, at a first known position along the extent of travel wherein when in the first known position, the arm contact member is out of contact with the gauge wheel arm;
  detecting that the row unit is positioned so the gauge wheel and the opener are in a known position relative to one another;
  controlling the planting depth actuator to move the arm contact member from the first known position to a second position, wherein when in the second position, the arm contact member contacts the gauge wheel arm;
  identifying how far the arm contact member moved along the extent of travel from the first known position to the second position, to identify the second position as a first calibration point; and
  adjusting a control curve, used to position the arm contact member to control planting depth of the row unit, based on the first calibration point.

2. The method of claim 1 wherein controlling the planting depth actuator to position the arm contact member at the first known position along the extent of travel, comprises:
  controlling the planting depth actuator to move the arm contact member to a first end of the extent of travel.

3. The method of claim 2 and further comprising:
  detecting when the arm contact member is in contact with the gauge wheel arm.

4. The method of claim 3 wherein detecting when the arm contact member is in contact with the gauge wheel arm comprises:
  detecting an increase in torque output by the planting depth actuator.

5. The method of claim 3 wherein the planting depth actuator comprises a motor with a rotatable output shaft that drives rotation of a lead screw that rotates to drive the arm contact member along an axis of movement and wherein controlling the planting depth actuator to move the arm contact member from the first known position to the second position, comprises:
  controlling the motor to rotate the rotatable output shaft.

6. The method of claim 5 wherein identifying how far the arm contact member moved comprises:
  counting a number of rotations of the rotatable output shaft and identifying how far the arm contact member moved based on the number of rotations and a pitch of the lead screw.

7. The method of claim 5 wherein the rotatable output shaft is coupled to the lead screw through a gear mechanism having a gear ratio and wherein identifying how far the arm contact member moved comprises:
  counting the number of rotations of the rotatable output shaft and identifying how far the arm contact member moved based on the number of rotations and the pitch of the lead screw and the gear ratio.

8. The method of claim 1 and further comprising:
  identifying wear of the opener and the gauge wheel based on the first calibration point.

9. The method of claim 8 and further comprising:
  sensing a position of the gauge wheel and wherein identifying wear comprises identifying wear of the opener and the gauge wheel, separately, based on the position of the gauge wheel and the first calibration point.

10. A planting depth control system, comprising:
  a control signal generator logic that generates control signals to control an actuator to position an arm contact member along a path of movement through an extent of travel and that contacts a gauge wheel arm to change a relative position of a gauge wheel relative to an opener on a planter row unit;
a position detector detecting that the row unit is positioned so the gauge wheel and the opener are in a known position relative to one another;
an arm contact member positioning logic that generates a position output to the control signal generator logic to:
position the arm contact member at a first known position along the extent of travel, wherein when in the first known position, the arm contact member is out of contact with the gauge wheel arm; and
move the arm contact member from the first known position to a second position in which the arm contact member contacts with the gauge wheel arm;
a planting depth calibration system that identifies how far the arm contact member moved along the extent of travel from the first known position to the second position, to identify the second position as a first calibration point; and
a control curve adjustment logic that adjusts a control curve, used to position the arm contact member to control planting depth of the row unit, based on the first calibration point.

11. The planting depth control system of claim 10 wherein the control signal generator logic is configured to control the actuator to position the arm contact member at the first known position, by controlling the actuator to move the arm contact member to a first end of the extent of travel.

12. The planting depth control system of claim 11 and further comprising:
a first position detector configured to detect when the arm contact member is in contact with the gauge wheel arm.

13. The planting depth control system of claim 12 wherein the first position detector comprises:
motor torque sensing logic detecting an increase in torque output by the actuator.

14. The planting depth control system of claim 12 wherein the actuator comprises a motor with a rotatable output shaft that drives rotation of a lead screw that rotates to drive the arm contact member along an axis of movement and wherein the planting depth calibration system, comprises:
motor revolution tracking logic configured to track a number of revolutions of the rotatable output shaft; and
arm contact member position detection logic identifying how far the arm contact member moved based on the number of revolutions and a pitch of the lead screw.

15. The planting depth control system of claim 14 and further comprising arm contact member position detection logic; and
wherein the rotatable output shaft is coupled to the lead screw through a gear mechanism having a gear ratio and wherein the arm contact member position detection logic is configured to identify how far the arm contact member moved based on the number of revolutions and the pitch of the lead screw and the gear ratio.

16. The planting depth control system of claim 10 and further comprising:
wear identifying logic configured to identify wear of the opener and the gauge wheel based on the first calibration point.

17. The planting depth control system of claim 16 and further comprising:
a gauge wheel position sensor sensing a position of the gauge wheel and wherein the wear identifying logic identifies wear of the opener and the gauge wheel, separately, based on the position of the gauge wheel and the first calibration point.

18. A method of controlling a planting depth actuator, comprising:
controlling the planting depth actuator to position an arm contact member, that moves along a path of movement through an extent of travel and that contacts a gauge wheel arm to change a relative position of a gauge wheel relative to an opener on a planter row unit, at a first end position along the extent of travel wherein when in the first end position, the arm contact member is out of contact with the gauge wheel arm;
detecting that the row unit is positioned so a lowest position of the gauge wheel and a lowest position of the opener are in a known position relative to one another;
controlling the planting depth actuator to move the arm contact member from the first end position to a second position in which the arm contact member contacts the gauge wheel arm;
identifying how far the arm contact member moved along the extent of travel from the first end position to the second position, to identify the second position as a first calibration point; and
adjusting a control curve, used to position the arm contact member to control planting depth of the row unit, based on the first calibration point.

19. The method of claim 18 wherein the actuator comprises a motor with a rotatable output shaft that drives rotation of a lead screw that rotates to drive the arm contact member along an axis of movement and wherein controlling the actuator to move the arm contact member from the first end position to the second position comprises controlling the motor to rotate the rotatable output shaft and wherein identifying how far the arm contact member moved comprises:
counting a number of rotations of the rotatable output shaft and identifying how far the arm contact member moved based on the number of rotations and a pitch of the lead screw.

20. The method of claim 19 and further comprising:
sensing a position of the gauge wheel; and
identifying wear of the opener and the gauge wheel, separately, based on the position of the gauge wheel and the first calibration point.

* * * * *